(12) United States Patent  (10) Patent No.: US 8,124,604 B2
Dewdney et al.  (45) Date of Patent: *Feb. 28, 2012

(54) INHIBITORS OF BRUTON'S TYROSINE KINASE

(75) Inventors: Nolan James Dewdney, Saratoga, CA (US); Rama K. Kondru, Morris Plains, NJ (US); Bradley E. Loe, Santa Cruz, CA (US); Yan Lou, Clifton, NJ (US); Joel McIntosh, Pacifica, CA (US); Timothy D. Owens, Jersey City, NJ (US); Michael Soth, Glen Rock, NJ (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/987,187

(22) Filed: Jan. 10, 2011

(65) Prior Publication Data

US 2011/0105479 A1  May 5, 2011

Related U.S. Application Data

(62) Division of application No. 12/456,911, filed on Jun. 24, 2009, now Pat. No. 7,902,194.

(60) Provisional application No. 61/075,277, filed on Jun. 24, 2008.

(51) Int. Cl.
C07D 401/14 (2006.01)
C07D 413/14 (2006.01)
A61K 31/5355 (2006.01)
A61K 31/513 (2006.01)

(52) U.S. Cl. ................ 514/234.8; 514/266.21; 544/119; 544/284

(58) Field of Classification Search ........................ None
See application file for complete search history.

(56) References Cited

U.S. PATENT DOCUMENTS

| 7,943,618 B2 * | 5/2011 | Dewdney et al. ........ 514/252.01 |
| 2008/0153834 A1 | 6/2008 | Blomgren et al. |

FOREIGN PATENT DOCUMENTS

| WO | 2004/022562 | 3/2004 |
| WO | 2005/014599 | 2/2005 |
| WO | 2006099075 | 9/2006 |
| WO | 2006124731 | 11/2006 |
| WO | 2007021795 | 2/2007 |
| WO | 2007027528 | 3/2007 |
| WO | 2007027594 | 3/2007 |
| WO | 2007027729 | 3/2007 |
| WO | 2007136465 | 11/2007 |
| WO | 2008033854 | 3/2008 |
| WO | 2008033857 | 3/2008 |
| WO | 2008033858 | 3/2008 |
| WO | 2009039397 | 3/2009 |
| WO | 2009053269 | 4/2009 |
| WO | 2009/077334 | 6/2009 |

OTHER PUBLICATIONS

Hunter, T. Cell (1987) 50:823-829.
Rastetter, et al., Annu. Rev. Med (2004) 55:477-503.
Khan, et al., Immunity (1995) 3:283-299.
Ellmeier, et al., J. Exp. Med. (2000) 192:1611-1623.
Rosen, et al., New Eng. J. Med. (1995) 333:431.
Lindvall, et al., Immunol. Rev. (2005) 203:200-215.
Jansson and Holmdahl, Clin. Exp. Immunol. (1993) 94:459-465.
Pan, Z., et al., Chem. Med. Chem. (2007) 2:58-61.
Iwaki, et al., J. Biol. Chem. (2005) 280:40261-40270.
Horwood, et al., J. Exp. Med. (2003) 197:1603-1611.
Islam and Smith, Immunol. Rev. (2000) 178:49-63.
Feldhahn, et al., J. Exp. Med. (2005) 201:1837-1852.
Vassilev, et al., J. Biol. Chem. (1998) 274, 1646-1656.

* cited by examiner

*Primary Examiner* — Rebecca Anderson
*Assistant Examiner* — Alicia L Otton
(74) *Attorney, Agent, or Firm* — George W. Johnston; Dennis P. Tramaloni; Jennifer L. Kisko

(57) ABSTRACT

This application discloses 5-phenyl-1H-pyridin-2-one and 6-phenyl-2H-pyridazin-3-one derivatives according to generic Formulae I-IV:

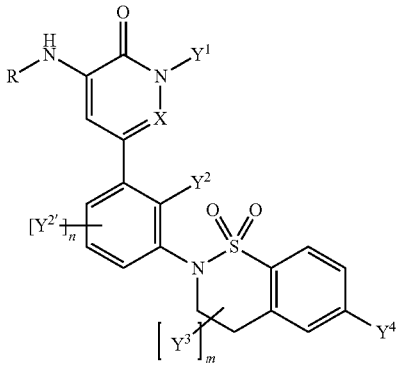

IV wherein, variables R, X, $Y^1$, $Y^2$, $Y^{2'}$, $Y^3$, $Y^4$, n and m are defined as described herein, which inhibit Btk. The compounds disclosed herein are useful to modulate the activity of Btk and treat diseases associated with excessive Btk activity. The compounds are further useful to treat inflammatory and auto immune diseases associated with aberrant B-cell proliferation such as rheumatoid arthritis. Also disclosed are compositions comprising compounds of Formulae I-IV and at least one carrier, diluent or excipient.

23 Claims, No Drawings

INHIBITORS OF BRUTON'S TYROSINE KINASE

CROSS-REFERENCE TO RELATED APPLICATIONS

This application is a divisional of U.S. patent application Ser. No. 12/456,911, filed on Jun. 24, 2009, and is entitled to the benefit of U.S. provisional patent application Ser. No. 61/075,277 filed on Jun. 24, 2008, the disclosure of which is incorporated herein by reference.

FIELD OF THE INVENTION

The present invention relates to the use of novel derivatives which inhibit Btk and are useful for the treatment of autoimmune and inflammatory diseases caused by aberrant B-cell activation. The novel 5-phenyl-1H-pyridin-2-one and 6-phenyl-2H-pyridazin-3-one derivatives described herein are useful for the treatment of arthritis.

BACKGROUND OF THE INVENTION

Protein kinases constitute one of the largest families of human enzymes and regulate many different signaling processes by adding phosphate groups to proteins (T. Hunter, Cell 1987 50:823-829). Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a target to modulate cellular function with small molecular kinase inhibitors and thus make good drug design targets. In addition to treatment of kinase-mediated disease processes, selective and efficacious inhibitors of kinase activity are also useful for investigation of cell signaling processes and identification of other cellular targets of therapeutic interest.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. *Annu Rev Med* 2004 55:477). Therefore inhibitors of the protein kinases that play a role in B-cell activation should be useful therapeutics for B-cell mediated disease pathology such as autoantibody production.

Signaling through the B-cell receptor (BCR) controls a range of B-cell responses including proliferation and differentiation into mature antibody producing cells. The BCR is a key regulatory point for B-cell activity and aberrant signaling can cause deregulated B-cell proliferation and formation of pathogenic autoantibodies that lead to multiple autoimmune and/or inflammatory diseases. Bruton's Tyrosine Kinase (Btk) is a non-BCR associated kinase that is membrane proximal and immediately downstream from BCR. Lack of Btk has been shown to block BCR signaling and therefore inhibition of Btk could be a useful therapeutic approach to block B-cell mediated disease processes.

Btk is a member of the Tec family of tyrosine kinases, and has been shown to be a critical regulator of early B-cell development and mature B-cell activation and survival (Khan et al. *Immunity* 1995 3:283; Ellmeier et al. *J. Exp. Med.* 2000 192:1611). Mutation of Btk in humans leads to the condition X-linked agammaglobulinemia (XLA) (reviewed in Rosen et al. *New Eng. J. Med.* 1995 333:431 and Lindvall et al. *Immunol. Rev.* 2005 203:200). These patients are immunocompromised and show impaired maturation of B-cells, decreased immunoglobulin and peripheral B-cell levels, diminished T-cell independent immune responses as well as attenuated calcium mobilization following BCR stimulation.

Evidence for a role for Btk in autoimmune and inflammatory diseases has also been provided by Btk-deficient mouse models. In preclinical murine models of systemic lupus erythematosus (SLE), Btk-deficient mice show marked amelioration of disease progression. In addition, Btk-deficient mice are resistant to collagen-induced arthritis (Jansson and Holmdahl *Clin. Exp. Immunol.* 1993 94:459). A selective Btk inhibitor has been demonstrated dose-dependent efficacy in a mouse arthritis model (Z. Pan et al., *Chem. Med. Chem.* 2007 2:58-61).

Btk is also expressed by cells other than B-cells that may be involved in disease processes. For example, Btk is expressed by mast cells and Btk-deficient bone marrow derived mast cells demonstrate impaired antigen induced degranulation (Iwaki et al. *J. Biol. Chem.* 2005 280:40261). This shows Btk could be useful to treat pathological mast cells responses such as allergy and asthma. Also monocytes from XLA patients, in which Btk activity is absent, show decreased TNF alpha production following stimulation (Horwood et al. *J Exp Med* 197:1603, 2003). Therefore TNF alpha mediated inflammation could be modulated by small molecular Btk inhibitors. Also, Btk has been reported to play a role in apoptosis (Islam and Smith *Immunol. Rev.* 2000 178:49,) and thus Btk inhibitors would be useful for the treatment of certain B-cell lymphomas and leukemias (Feldhahn et al. *J. Exp. Med.* 2005 201:1837,).

SUMMARY OF THE INVENTION

The present application provides the Btk inhibitor compounds of Formulae I-IV, methods of use thereof, as described herein below:

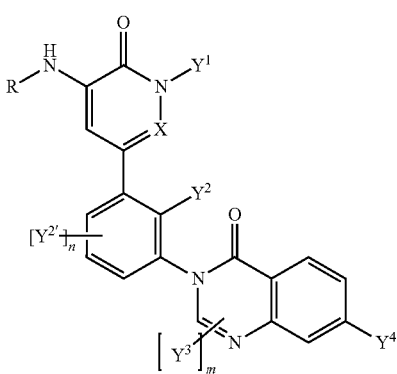

I

The application provides a compound of Formula I, wherein:

R is H, —R¹, —R¹—R²—R³, —R¹—R³, or —R²—R³;

R¹ is aryl, heteroaryl, cycloalkyl, or heterocycloalkyl, and is optionally substituted with R¹';

R¹' is lower alkyl, hydroxy, lower hydroxyalkyl, lower alkoxy, halogen, nitro, amino, cycloalkyl, heterocycloalkyl, cyano, or lower haloalkyl;

R² is —C(=O), —C(=O)O, —C(=O)N(R²'), —(CH$_2$)$_q$, or —S(=O)$_2$;

R²' is H or lower alkyl;

q is 1, 2, or 3;

R³ is H or R⁴;

R⁴ is lower alkyl, lower alkoxy, lower heteroalkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with one or more lower alkyl, hydroxy, oxo, lower hydroxyalkyl, lower alkoxy, halogen, nitro, amino, cyano, lower alkylsulfonyl, or lower haloalkyl;

X is CH or N,

Y¹ is H or lower alkyl;

Y² is Y²ᵃ or Y²ᵇ;

Y²ᵃ is H or halogen;

Y²ᵇ is lower alkyl, optionally substituted with one or more Y²ᵇ';

Y²ᵇ' is hydroxy, lower alkoxy, or halogen;

each Y²' is independently Y²'ᵃ or Y²'ᵇ;

Y²'ᵃ is halogen;

Y²'ᵇ is lower alkyl, optionally substituted with one or more Y²'ᵇ';

Y²'ᵇ' is hydroxy, lower alkoxy, or halogen;

n is 0, 1, 2, or 3;

Y³ is H, halogen, or lower alkyl, wherein lower alkyl is optionally substituted with one or more substituents selected from the group consisting of hydroxy, lower alkoxy, amino, and halogen;

m is 0 or 1;

Y⁴ is Y⁴ᵃ, Y⁴ᵇ, Y⁴ᶜ, or Y⁴ᵈ;

Y⁴ᵃ is H or halogen;

Y⁴ᵇ is lower alkyl, optionally substituted with one or more substituents selected from the group consisting of lower haloalkyl, halogen, hydroxy, amino, cyano and lower alkoxy;

Y⁴ᶜ is lower cycloalkyl, optionally substituted with one or more substituents selected from the group consisting of lower alkyl, lower haloalkyl, halogen, hydroxy, amino, and lower alkoxy; and Y⁴ᵈ is amino, optionally substituted with one or more lower alkyl;

or a pharmaceutically acceptable salt thereof.

The application provides a compound of Formula I, wherein Y¹ is methyl.

The application provides a compound of Formula I, wherein X is CH.

The application provides a compound of Formula I, wherein m is 0 and n is 0.

The application provides a compound of Formula I, wherein Y² is hydroxymethyl.

The application provides a compound of Formula I, wherein Y² is hydroxymethyl, Y¹ is methyl, m is 0 and n is 0.

The application provides a compound of Formula I, wherein X is CH, Y² is hydroxymethyl, Y¹ is methyl, m is 0 and n is 0.

The application provides a compound of Formula I, wherein Y⁴ is

wherein, $Y^5$ is H, halogen, lower alkyl, or lower haloalkyl.

The application provides a compound of Formula I, wherein $Y^4$ is

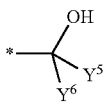

wherein, $Y^5$ and $Y^6$ are independently H, lower alkyl, or lower haloalkyl.

The application provides a compound of Formula I, wherein $Y^4$ is

wherein, $Y^5$ and $Y^6$ are independently H or lower alkyl.

The application provides a compound of Formula I, wherein $Y^4$ is

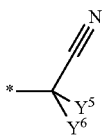

wherein, $Y^5$ and $Y^6$ are independently H, lower alkyl, or lower haloalkyl.

The application provides a compound of Formula I, wherein

R is $-R^1-R^2-R^3$;
$R^1$ is phenyl or pyridyl;
$R^2$ is $-C(=O)$;
$R^3$ is $R^4$; and
$R^4$ is morpholine or piperazine, optionally substituted with one or more lower alkyl.

The application provides a compound of Formula II,

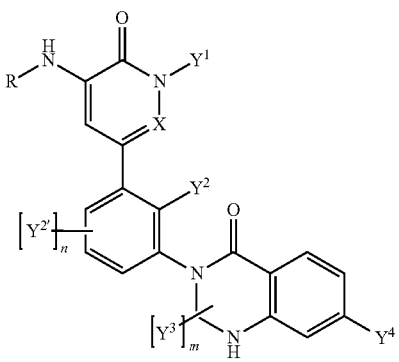

wherein:

R is H, $-R^1$, $-R^1-R^2-R^3$, $-R^1-R^3$, $-R^2$ or $-R^2-R^3$;

$R^1$ is aryl, heteroaryl, cycloalkyl, or heterocycloalkyl, and is optionally substituted with $R^{1'}$;

$R^{1'}$ is lower alkyl, hydroxy, lower hydroxyalkyl, lower alkoxy, halogen, nitro, amino, cycloalkyl, heterocycloalkyl, cyano, or lower haloalkyl;

$R^2$ is $-C(=O)$, $-C(=O)O$, $-C(=O)N(R^{2'})$, $-(CH_2)_q$, or $-S(=O)_2$;

$R^{2'}$ is H or lower alkyl;

q is 1, 2, or 3;

$R^3$ is H or $R^4$;

$R^4$ is lower alkyl, lower alkoxy, lower heteroalkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with one or more lower alkyl, hydroxy, oxo, lower hydroxyalkyl, lower alkoxy, halogen, nitro, amino, cyano, lower alkylsulfonyl, or lower haloalkyl;

X is CH or N;

$Y^1$ is H or lower alkyl;

$Y^2$ is $Y^{2a}$ or $Y^{2b}$;

$Y^{2a}$ is H or halogen;

$Y^{2b}$ is lower alkyl, optionally substituted with one or more $Y^{2b'}$;

$Y^{2b'}$ is hydroxy, lower alkoxy, or halogen;

each $Y^{2'}$ is independently $Y^{2'a}$ or $Y^{2'b}$;

$Y^{2'a}$ is halogen;

$Y^{2'b}$ is lower alkyl, optionally substituted with one or more $Y^{2'b'}$;

$Y^{2'b'}$ is hydroxy, lower alkoxy, or halogen;

n is 0, 1, 2, or 3.

$Y^3$ is H, halogen, or lower alkyl, wherein lower alkyl is optionally substituted with one or more substituents selected from the group consisting of hydroxy, lower alkoxy, amino, and halogen;

m is 0 or 1;

$Y^4$ is $Y^{4a}$, $Y^{4b}$, $Y^{4c}$, or $Y^{4d}$;

$Y^{4a}$ is H or halogen;

$Y^{4b}$ is lower alkyl, optionally substituted with one or more substituents selected from the group consisting of lower haloalkyl, halogen, hydroxy, amino, cyano and lower alkoxy;

$Y^{4c}$ is lower cycloalkyl, optionally substituted with one or more substituents selected from the group consisting of lower alkyl, lower haloalkyl, halogen, hydroxy, amino, and lower alkoxy; and $Y^{4d}$ is amino, optionally substituted with one or more lower alkyl;

or a pharmaceutically acceptable salt thereof.

The application provides a compound of Formula II, wherein $Y^1$ is methyl.

The application provides a compound of Formula II, wherein X is CH.

The application provides a compound of Formula II, wherein m is 0 and n is 0.

The application provides a compound of Formula II, wherein $Y^2$ is hydroxymethyl.

The application provides a compound of Formula II, wherein $Y^4$ is

wherein, $Y^5$ is H, halogen, lower alkyl, or lower haloalkyl.

The application provides a compound of Formula III,

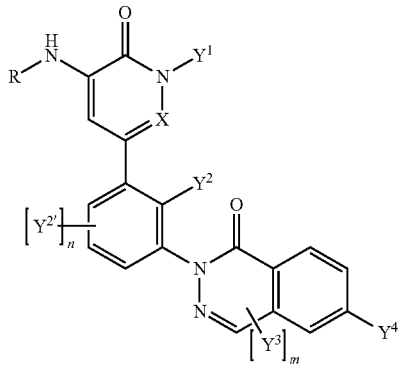

III wherein:
R is H, —$R^1$, —$R^1$—$R^2$—$R^3$, —$R^1$—$R^3$, —$R^2$ or —$R^2$—$R^3$;
  $R^1$ is aryl, heteroaryl, cycloalkyl, or heterocycloalkyl, and is optionally substituted with $R^{1'}$;
    $R^{1'}$ is lower alkyl, hydroxy, lower hydroxyalkyl, lower alkoxy, halogen, nitro, amino, cycloalkyl, heterocycloalkyl, cyano, or lower haloalkyl;
  $R^2$ is —C(=O), —C(=O)O, —C(=O)N($R^{2'}$), —(CH$_2$)$_q$, or —S(=O)$_2$;
    $R^{2'}$ is H or lower alkyl;
    q is 1, 2, or 3;
  $R^3$ is H or $R^4$;
  $R^4$ is lower alkyl, lower alkoxy, lower heteroalkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with one or more lower alkyl, hydroxy, oxo, lower hydroxyalkyl, lower alkoxy, halogen, nitro, amino, cyano, lower alkylsulfonyl, or lower haloalkyl;
X is CH or N;
$Y^1$ is H or lower alkyl;
$Y^2$ is $Y^{2a}$ or $Y^{2b}$;
  $Y^{2a}$ is H or halogen;
  $Y^{2b}$ is lower alkyl, optionally substituted with one or more $Y^{2b'}$;
    $Y^{2b'}$ is hydroxy, lower alkoxy, or halogen;
each $Y^{2'}$ is independently $Y^{2'a}$ or $Y^{2'b}$;
  $Y^{2'a}$ is halogen;
  $Y^{2'b}$ is lower alkyl, optionally substituted with one or more $Y^{2'b'}$;
    $Y^{2'b'}$ is hydroxy, lower alkoxy, or halogen;
n is 0, 1, 2, or 3.
$Y^3$ is H, halogen, or lower alkyl, wherein lower alkyl is optionally substituted with one or more substituents selected from the group consisting of hydroxy, lower alkoxy, amino, and halogen;

m is 0 or 1;
$Y^4$ is $Y^{4a}$, $Y^{4b}$, $Y^{4c}$, or $Y^{4d}$;
  $Y^{4a}$ is H or halogen;
  $Y^{4b}$ is lower alkyl, optionally substituted with one or more substituents selected from the group consisting of haloalkyl, halogen, hydroxy, amino, cyano and lower alkoxy;
  $Y^{4c}$ is lower cycloalkyl, optionally substituted with one or more substituents selected from the group consisting of lower alkyl, lower haloalkyl, halogen, hydroxy, amino, and lower alkoxy; and
  $Y^{4d}$ is amino, optionally substituted with one or more lower alkyl;
or a pharmaceutically acceptable salt thereof.

The application provides a compound of Formula III, wherein $Y^1$ is methyl and X is CH.

The application provides a compound of Formula III, wherein m is 0 and n is 0.

The application provides a compound of Formula III, wherein $Y^2$ is hydroxymethyl.

The application provides a compound of Formula IV,

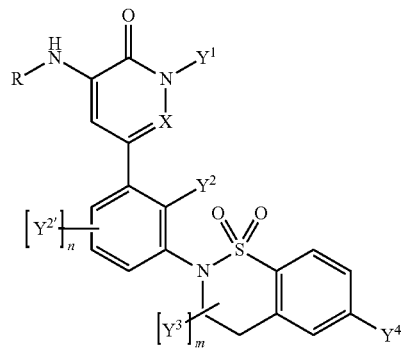

IV wherein:
R is H, —$R^1$, —$R^1$—$R^2$—$R^3$, —$R^1$—$R^3$, —$R^2$ or —$R^2$—$R^3$;
  $R^1$ is aryl, heteroaryl, cycloalkyl, or heterocycloalkyl, and is optionally substituted with $R^{1'}$;
    $R^{1'}$ is lower alkyl, hydroxy, lower hydroxyalkyl, lower alkoxy, halogen, nitro, amino, cycloalkyl, heterocycloalkyl, cyano, or lower haloalkyl;
  $R^2$ is —C(=O), —C(=O)O, —C(=O)N($R^{2'}$), —(CH$_2$)$_q$, or —S(=O)$_2$;
    $R^{2'}$ is H or lower alkyl;
    q is 1, 2, or 3;
  $R^3$ is H or $R^4$;
  $R^4$ is lower alkyl, lower alkoxy, lower heteroalkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with one or more lower alkyl, hydroxy, oxo, lower hydroxyalkyl, lower alkoxy, halogen, nitro, amino, cyano, lower alkylsulfonyl, or lower haloalkyl;
X is CH or N;
$Y^1$ is H or lower alkyl;
$Y^2$ is $Y^{2a}$ or $Y^{2b}$;
  $Y^{2a}$ is H or halogen;
  $Y^{2b}$ is lower alkyl, optionally substituted with one or more $Y^{2b'}$;
    $Y^{2b'}$ is hydroxy, lower alkoxy, or halogen;
each $Y^{2'}$ is independently $Y^{2'a}$ or $Y^{2'b}$;

$Y^{2'a}$ is halogen;
$Y^{2'b}$ is lower alkyl, optionally substituted with one or more $Y^{2'b'}$;
$Y^{2'b'}$ is hydroxy, lower alkoxy, or halogen;
n is 0, 1, 2, or 3.
$Y^3$ is H, halogen, or lower alkyl, wherein lower alkyl is optionally substituted with one or more substituents selected from the group consisting of hydroxy, lower alkoxy, amino, and halogen;
m is 0 or 1;
$Y^4$ is $Y^{4a}$, $Y^{4b}$, $Y^{4c}$, or $Y^{4d}$;
  $Y^{4a}$ is H or halogen;
  $Y^{4b}$ is lower alkyl, optionally substituted with one or more substituents selected from the group consisting of lower haloalkyl, halogen, hydroxy, amino, cyano and lower alkoxy;
  $Y^{4c}$ is lower cycloalkyl, optionally substituted with one or more substituents selected from the group consisting of lower alkyl, lower haloalkyl, halogen, hydroxy, amino, and lower alkoxy; and
  $Y^{4d}$ is amino, optionally substituted with one or more lower alkyl;
or a pharmaceutically acceptable salt thereof.

The application provides a compound of Formula IV, wherein $Y^1$ is methyl and X is CH.

The application provides a compound of Formula IV, wherein m is 0 and n is 0.

The application provides a compound of Formula IV, wherein $Y^2$ is hydroxymethyl.

The application provides a compound selected from the group consisting of:
1-{5-[3-(7-tert-Butyl-4-oxo-4H-quinazolin-3-yl)-2-methyl-phenyl]-1-methyl-2-oxo-1,2-dihydro-pyridin-3-yl}-3-methyl-urea;
7-Dimethylamino-3-(2-methyl-3-{1-methyl-5-[5-(morpholine-4-carbonyl)-pyridin-2-ylamino]-6-oxo-1,6-dihydro-pyridin-3-yl}-phenyl)-3H-quinazolin-4-one;
7-tert-Butyl-3-(2-methyl-3-{1-methyl-5-[5-(morpholine-4-carbonyl)-pyridin-2-ylamino]-6-oxo-1,6-dihydro-pyridazin-3-yl}-phenyl)-3H-quinazolin-4-one;
7-Dimethylamino-3-(2-methyl-3-{1-methyl-5-[5-(morpholine-4-carbonyl)-pyridin-2-ylamino]-6-oxo-1,6-dihydro-pyridin-3-yl}-phenyl)-2,3-dihydro-1H-quinazolin-4-one;
1-{5-[3-(7-Dimethylamino-4-oxo-1,4-dihydro-2H-quinazolin-3-yl)-2-methyl-phenyl]-1-methyl-2-oxo-1,2-dihydro-pyridin-3-yl}-3-methyl-urea;
7-(1-Hydroxy-1-methyl-ethyl)-3-(2-methyl-3-{1-methyl-5-[5-(morpholine-4-carbonyl)-pyridin-2-ylamino]-6-oxo-1,6-dihydro-pyridin-3-yl}-phenyl)-2,3-dihydro-1H-quinazolin-4-one;
7-tert-Butyl-3-(2-methyl-3-{1-methyl-5-[5-(morpholine-4-carbonyl)-pyridin-2-ylamino]-6-oxo-1,6-dihydro-pyridazin-3-yl}-phenyl)-2,3-dihydro-1H-quinazolin-4-one;
6-Dimethylamino-2-(2-methyl-3-{1-methyl-5-[5-(morpholine-4-carbonyl)-pyridin-2-ylamino]-6-oxo-1,6-dihydro-pyridin-3-yl}-phenyl)-2H-phthalazin-1-one;
6-Dimethylamino-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-phthalazin-1-one;
6-Dimethylamino-2-{2-hydroxymethyl-3-[1-methyl-5-(5-morpholin-4-yl-pyridin-2-ylamino)-6-oxo-1,6-dihydro-pyridin-3-yl]-phenyl}-2H-phthalazin-1-one;
6-tert-Butyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-phthalazin-1-one;
6-tert-Butyl-2-{2-hydroxymethyl-3-[1-methyl-5-(5-morpholin-4-yl-pyridin-2-ylamino)-6-oxo-1,6-dihydro-pyridin-3-yl]-phenyl}-2H-phthalazin-1-one;
6-tert-Butyl-2-[2-hydroxymethyl-3-(5-{5-[4-(2-methoxy-ethyl)-piperazin-1-yl]-pyridin-2-ylamino}-1-methyl-6-oxo-1,6-dihydro-pyridin-3-yl)-phenyl]-2H-phthalazin-1-one
6-Dimethylamino-2-[2-hydroxymethyl-3-(5-{5-[4-(2-methoxy-ethyl)-piperazin-1-yl]-pyridin-2-ylamino}-1-methyl-6-oxo-1,6-dihydro-pyridin-3-yl)-phenyl]-2H-phthalazin-1-one;
6-Dimethylamino-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-phthalazin-1-one;
2-(3-{5-[5-(4-Acetyl-piperazin-1-yl)-pyridin-2-ylamino]-1-methyl-6-oxo-1,6-dihydro-pyridin-3-yl}-2-hydroxymethyl-phenyl)-6-tert-butyl-2H-phthalazin-1-one;
2-(3-{5-[5-(4-Acetyl-piperazin-1-yl)-pyridin-2-ylamino]-1-methyl-6-oxo-1,6-dihydro-pyridin-3-yl}-2-hydroxymethyl-phenyl)-6-dimethylamino-2H-phthalazin-1-one;
6-tert-Butyl-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-phthalazin-1-one;
6-tert-Butyl-2-(3-{5-[5-(4-ethyl-piperazin-1-yl)-pyridin-2-ylamino]-1-methyl-6-oxo-1,6-dihydro-pyridin-3-yl}-2-hydroxymethyl-phenyl)-2H-phthalazin-1-one;
6-tert-Butyl-2-{2-hydroxymethyl-3-[1-methyl-6-oxo-5-(5-piperazin-1-yl-pyridin-2-ylamino)-1,6-dihydro-pyridin-3-yl]-phenyl}-2H-phthalazin-1-one;
4-(6-{5-[3-(6-tert-Butyl-1-oxo-1H-phthalazin-2-yl)-2-hydroxymethyl-phenyl]-1-methyl-2-oxo-1,2-dihydro-pyridin-3-ylamino}-pyridin-3-yl)-piperazine-1-carboxylic acid tert-butyl ester;
5-[3-(6-Bromo-1,1-dioxo-3,4-dihydro-1H-1λ6-benzo[e][1,2]thiazin-2-yl)-2-hydroxymethyl-phenyl]-1-methyl-3-[5-(morpholine-4-carbonyl)-pyridin-2-ylamino]-1H-pyridin-2-one;
5-[3-(6-Cyclopropyl-1,1-dioxo-3,4-dihydro-1H-1λ6-benzo[e][1,2]thiazin-2-yl)-2-hydroxymethyl-phenyl]-1-methyl-3-[5-(morpholine-4-carbonyl)-pyridin-2-ylamino]-1H-pyridin-2-one;
5-[3-(6-Dimethylamino-1,1-dioxo-3,4-dihydro-1H-1λ6-benzo[e][1,2]thiazin-2-yl)-2-hydroxymethyl-phenyl]-1-methyl-3-[5-(morpholine-4-carbonyl)-pyridin-2-ylamino]-1H-pyridin-2-one; and
5-[3-(6-Fluoro-1,1-dioxo-3,4-dihydro-1H-1λ6-benzo[e][1,2]thiazin-2-yl)-2-hydroxymethyl-phenyl]-1-methyl-3-[5-(morpholine-4-carbonyl)-pyridin-2-ylamino]-1H-pyridin-2-one.

The application provides a method for treating an inflammatory and/or autoimmune condition comprising administering to a patient in need thereof a therapeutically effective amount of the Btk inhibitor compound of any one of Formulae I-IV.

The application provides a method for treating arthritis comprising administering to a patient in need thereof a therapeutically effective amount of the Btk inhibitor compound of any one of Formulae I-IV.

The application provides a method for treating rheumatoid arthritis comprising administering to a patient in need thereof a therapeutically effective amount of the Btk inhibitor compound of any one of the above Formulae or variations thereof.

The application provides a method for treating asthma comprising administering to a patient in need thereof a therapeutically effective amount of the Btk inhibitor compound of any one of the above Formulae or variations thereof.

The application provides a method for treating lupus comprising administering to a patient in need thereof a therapeutically effective amount of the Btk inhibitor compound of any one of the above Formulae or variations thereof.

The application provides a compound of Formula I',

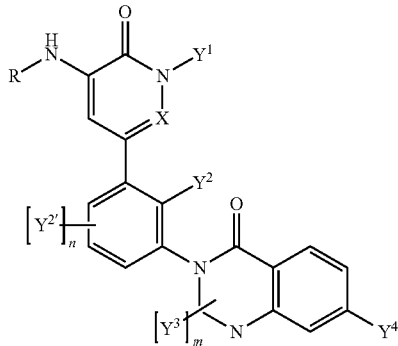

wherein:
R is H, —$R^1$, —$R^1$—$R^2$—$R^3$, —$R^1$—$R^3$, or —$R^2$—$R^3$;
  $R^1$ is aryl, heteroaryl, cycloalkyl, or heterocycloalkyl, and is optionally substituted with $R^{1'}$;
    $R^{1'}$ is lower alkyl, hydroxy, lower hydroxyalkyl, lower alkoxy, halogen, nitro, amino, cycloalkyl, heterocycloalkyl, cyano, or lower haloalkyl,
  $R^2$ is —C(=O), —C(=O)O, —C(=O)N($R^{2'}$), —$(CH_2)_q$, or —S(=O)$_2$;
    $R^{2'}$ is H or lower alkyl;
    q is 1, 2, or 3;
  $R^3$ is H or $R^4$;
  $R^4$ is lower alkyl, lower alkoxy, lower heteroalkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with one or more lower alkyl, hydroxy, oxo, lower hydroxyalkyl, lower alkoxy, halogen, nitro, amino, cyano, lower alkylsulfonyl, or lower haloalkyl;
X is CH or N;
$Y^1$ is H or lower alkyl;
$Y^2$ is $Y^{2a}$ or $Y^{2b}$;
  $Y^{2a}$ is H or halogen;
  $Y^{2b}$ is lower alkyl, optionally substituted with one or more $Y^{2b'}$;
    $Y^{2b'}$ is hydroxy, lower alkoxy, or halogen;
each $Y^{2'}$ is independently $Y^{2'a}$ or $Y^{2'b}$;
  $Y^{2'a}$ is halogen;
  $Y^{2'b}$ is lower alkyl, optionally substituted with one or more $Y^{2'b'}$;
    $Y^{2'b'}$ is hydroxy, lower alkoxy, or halogen;
n is 0, 1, 2, or 3.
$Y^3$ is H, halogen, or lower alkyl, wherein lower alkyl is optionally substituted with one or more substituents selected from the group consisting of hydroxy, lower alkoxy, amino, and halogen,
m is 0 or 1;
$Y^4$ is $Y^{4a}$, $Y^{4b}$, $Y^{4c}$, $Y^{4d}$;
  $Y^{4a}$ is H or halogen;
  $Y^{4b}$ is lower alkyl, optionally substituted with one or more substituents selected from the group consisting of lower haloalkyl, halogen, hydroxy, amino, and lower alkoxy;
  $Y^{4c}$ is lower cycloalkyl, optionally substituted with one or more substituents selected from the group consisting of lower alkyl, lower haloalkyl, halogen, hydroxy, amino, and lower alkoxy; and
  $Y^{4d}$ is amino, optionally substituted with one or more lower alkyl;
or a pharmaceutically acceptable salt thereof.

In one embodiment of Formula I', $Y^1$ is methyl.
In one embodiment of Formula I', X is N, n is 0 and m is 0.
In one embodiment of Formula I', $Y^1$ is methyl, X is N, n is 0 and m is 0.
In one embodiment of Formula I', $Y^1$ is methyl, X is N, n is 0, and m is 0.
In one embodiment of Formula I', $Y^2$ is hydroxymethyl.
In one embodiment of Formula I', $Y^1$ is methyl and $Y^2$ is hydroxymethyl.
In one embodiment of Formula I', $Y^1$ is methyl, $Y^2$ is hydroxymethyl, X is N, n is 0 and m is 0.
In one embodiment of Formula I', $Y^1$ is methyl, X is N, n is 0, and m is 0.
In one embodiment of Formula I', $Y^1$ is methyl, $Y^2$ is hydroxymethyl, X is N, n is 0 and m is 0.
In one embodiment of Formula I', $Y^2$ is methyl.
In one embodiment of Formula I', $Y^2$ is hydroxyethyl.
In one embodiment of Formula I', $Y^2$ is halogen.
In one embodiment of Formula I', X is CH, n is 0, and m is 0.
In one embodiment of Formula I', $Y^1$ is methyl, X is CH, n is 0, and m is 0.
In one embodiment of Formula I', $Y^1$ is methyl, $Y^2$ is hydroxymethyl, X is CH, n is 0 and m is 0.
In one embodiment of Formula I', $Y^1$ is methyl, $Y^2$ is methyl, X is CH, n is 0 and m is 0.
In one embodiment of Formula I', $Y^1$ is methyl, $Y^2$ is hydroxyethyl, X is CH, n is 0 and m is 0.
In one embodiment of Formula I', $Y^1$ is methyl, $Y^2$ is halogen, X is CH, n is 0 and m is 0
In one embodiment of Formula I', $Y^4$ is

wherein, $Y^5$ is H, halogen, lower alkyl, or lower haloalkyl.
In one embodiment of Formula I', $Y^1$ is methyl, $Y^2$ is hydroxymethyl, X is CH, n is 0, m is 0, and $Y^4$ is

wherein, $Y^5$ is H, halogen; lower alkyl, or lower haloalkyl.
In one variation of the above embodiment of Formula I',
R is —$R^1$—$R^2$—$R^3$;
$R^1$ is phenyl or pyridyl,
$R^2$ is —C(=O);
$R^3$ is $R^4$; and
$R^4$ is morpholine or piperazine, optionally substituted with one or more lower alkyl.
In one embodiment of Formula I', $Y^4$ is lower alkyl.
In one embodiment of Formula I', $Y^1$ is methyl, $Y^2$ is hydroxymethyl, X is CH, n is 0, m is 0, and $Y^4$ is lower alkyl.
In one variation of the above embodiment of Formula I',
R is —$R^1$—$R^2$—$R^3$;

$R^1$ is phenyl or pyridyl;
$R^2$ is —C(=O);
$R^3$ is $R^4$; and
$R^4$ is morpholine or piperazine, optionally substituted with one or more lower alkyl.

In another variation of the above embodiment of Formula I',
R is —$R^2$—$R^3$;
$R^2$ is —C(=O)NH;
$R^3$ is H or $R^4$; and
$R^4$ is lower alkyl.

In one embodiment of Formula I', $Y^4$ is

wherein, $Y^5$ and $Y^6$ are independently H, lower alkyl, or lower haloalkyl.

In one embodiment of Formula I', $Y^1$ is methyl, $Y^2$ is hydroxymethyl, X is CH, n is 0, m is 0, and $Y^4$ is

wherein, $Y^5$ and $Y^6$ are independently H, lower alkyl, or lower haloalkyl.

In one variation of the above embodiment of Formula I',
R is —$R^1$—$R^2$—$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

In one embodiment of Formula I', $Y^4$ is

wherein, $Y^5$ and $Y^6$ are independently H or lower alkyl.

In one embodiment of Formula I', $Y^1$ is methyl, $Y^2$ is hydroxymethyl, X is CH, n is 0, m is 0, and $Y^4$ is

wherein, $Y^5$ and $Y^6$ are independently H or lower alkyl.

In one variation of the above embodiment of Formula I',
R is —$R^2$—$R^3$;
$R^2$ is —C(=O)NH;
$R^3$ is H or $R^4$; and
$R^4$ is lower alkyl.

In another variation of the above embodiment of Formula I',
R is —$R^1$—$R^2$—$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

In one embodiment of Formula I', $Y^1$ is methyl, $Y^2$ is hydroxymethyl, X is CH, n is 0, m is 0, and $Y^4$ is

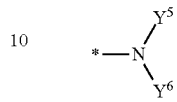

wherein, $Y^5$ and $Y^6$ are independently H or lower alkyl.

In one variation of the above embodiment of Formula I',
R is —$R^1$—$R^2$—$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

In one embodiment of Formula I', $Y^1$ is methyl, $Y^2$ is hydroxymethyl, X is N, n is 0, m is 0, and $Y^4$ is

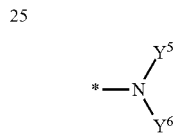

wherein, $Y^5$ and $Y^6$ are independently H or lower alkyl.

In one variation of the above embodiment of Formula I',
R is —$R^1$—$R^2$—$R^3$,
$R^1$ is phenyl or pyridyl;
$R^2$ is —C(=O);
$R^3$ is $R^4$; and
$R^4$ is morpholine or piperazine, optionally substituted with one or more lower alkyl.

In one embodiment of Formula I', $Y^1$ is methyl, $Y^2$ is hydroxymethyl, X is N, n is 0, in is 0, and $Y^4$ is

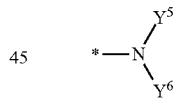

wherein, $Y^5$ and $Y^6$ are independently H or lower alkyl.

In one variation of the above embodiment of Formula I',
R is —$R^1$—$R^2$—$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

In one embodiment of Formula I', $Y^4$ is

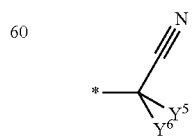

wherein, $Y^5$ and $Y^6$ are independently H, lower alkyl, or lower haloalkyl.

In one embodiment of Formula I', $Y^1$ is methyl, $Y^2$ is hydroxymethyl, X is CH, n is 0, m is 0, and $Y^4$ is

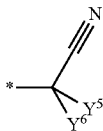

wherein, $Y^5$ and $Y^6$ are independently H, lower alkyl, or lower haloalkyl.

In one variation of the above embodiment of Formula I',
R is —$R^1$—$R^2$—$R^3$;
$R^1$ is phenyl or pyridyl;
$R^2$ is —C(=O);
$R^3$ is $R^4$, and
$R^4$ is morpholine or piperazine, optionally substituted with one or more lower alkyl.

The application provides a compound of Formula II',

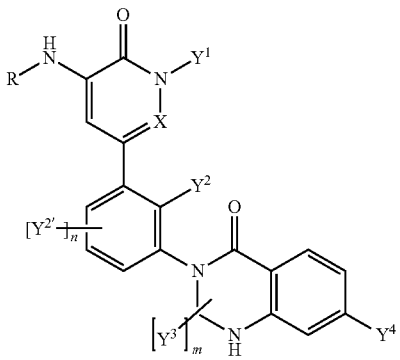

II' wherein:
R is H, —$R^1$, —$R^1$—$R^2$—$R^3$, —$R^1$—$R^3$, or —$R^2$—$R^3$;
   $R^1$ is aryl, heteroaryl, cycloalkyl, or heterocycloalkyl, and is optionally substituted with $R^{1'}$;
   $R^{1'}$ is lower alkyl, hydroxy, lower hydroxyalkyl, lower alkoxy, halogen, nitro, amino, cycloalkyl, heterocycloalkyl, cyano, or lower haloalkyl;
   $R^2$ is —C(=O), —C(=O)O, —C(=O)N($R^{2'}$), —(CH$_2$)$_q$, or —S(=O)$_2$;
     $R^{2'}$ is H or lower alkyl;
     q is 1, 2, or 3;
   $R^3$ is H or $R^4$;
   $R^4$ is lower alkyl, lower alkoxy, lower heteroalkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with one or more lower alkyl, hydroxy, oxo, lower hydroxyalkyl, lower alkoxy, halogen, nitro, amino, cyano, lower alkylsulfonyl, or lower haloalkyl;
X is CH or N;
$Y^1$ is H or lower alkyl;
$Y^2$ is $Y^{2a}$ or $Y^{2b}$;
   $Y^{2a}$ is H or halogen;
   $Y^{2b}$ is lower alkyl, optionally substituted with one or more $Y^{2b'}$;
   $Y^{2b'}$ is hydroxy, lower alkoxy, or halogen;
each $Y^{2'}$ is independently $Y^{2'a}$ or $Y^{2'b}$;
   $Y^{2'a}$ is halogen;
   $Y^{2'b}$ is lower alkyl, optionally substituted with one or more $Y^{2'b'}$;
   $Y^{2'b'}$ is hydroxy, lower alkoxy, or halogen;
n is 0, 1, 2, or 3.
$Y^3$ is H, halogen, or lower alkyl, wherein lower alkyl is optionally substituted with one or more substituents selected from the group consisting of hydroxy, lower alkoxy, amino, and halogen;
m is 0 or 1;
$Y^4$ is $Y^{4a}$, $Y^{4b}$, $Y^{4c}$, or $Y^{4d}$;
   $Y^{4a}$ is H or halogen;
   $Y^{4b}$ is lower alkyl, optionally substituted with one or more substituents selected from the group consisting of lower haloalkyl, halogen, hydroxy, amino, and lower alkoxy;
   $Y^{4c}$ is lower cycloalkyl, optionally substituted with one or more substituents selected from the group consisting of lower alkyl, lower haloalkyl, halogen, hydroxy, amino, and lower alkoxy; and
   $Y^{4d}$ is amino, optionally substituted with one or more lower alkyl;
or a pharmaceutically acceptable salt thereof.

In one embodiment of Formula II', $Y^1$ is methyl.
In one embodiment of Formula II', $Y^2$ is hydroxymethyl.
In one embodiment of Formula II', X is N.
In one embodiment of Formula II', X is N, n is 0 and m is 0.
In one embodiment of Formula II', $Y^2$ is hydroxymethyl, X is N, n is 0 and m is 0.
In one embodiment of Formula II', $Y^1$ is methyl, X is N, n is 0 and m is 0.
In one embodiment of Formula II', $Y^2$ is hydroxymethyl, $Y^1$ is methyl, X is N, n is 0 and m is 0.
In one embodiment of Formula II', $Y^2$ is methyl.
In one embodiment of Formula II', $Y^2$ is hydroxyethyl.
In one embodiment of Formula II', $Y^2$ is halogen.
In one embodiment of Formula II', X is CH.
In one embodiment of Formula II', X is CH, n is 0 and m is 0.
In one embodiment of Formula II', $Y^2$ is hydroxymethyl, X is CH, n is 0 and m is 0.
In one embodiment of Formula II', $Y^1$ is methyl, X is CH, n is 0 and m is 0.
In one embodiment of Formula II', $Y^2$ is hydroxymethyl, $Y^1$ is methyl, X is CH, n is 0 and m is 0.
In one embodiment of Formula II', $Y^4$ is

wherein, $Y^5$ is H, halogen, lower alkyl, or lower haloalkyl.
In one embodiment of Formula II', $Y^2$ is hydroxymethyl, $Y^1$ is methyl, X is CH, n is 0 and m is 0, and $Y^4$ is

wherein, $Y^5$ is H, halogen, lower alkyl, or lower haloalkyl.
In one variation of the above embodiment of Formula II'
R is —$R^1$—$R^2$—$R^3$;
$R^1$ is phenyl or pyridyl;
$R^2$ is —C(=O);
$R^3$ is $R^4$; and $R^4$ is morpholine or piperazine, optionally substituted with one or more lower alkyl.

In another variation of the above embodiment of Formula II',
R is —$R^2$—$R^3$;
$R^2$ is —C(=O)NH;
$R^3$ is H or $R^4$; and
$R^4$ is lower alkyl.

In yet another variation of the above embodiment of Formula II',
R is $R^1$; and
$R^1$ is pyrazolyl, optionally substituted with $R^{1'}$.

In one embodiment of Formula II', $Y^2$ is hydroxymethyl, $Y^1$ is methyl, X is CH, n is 0 and m is 0, and $Y^4$ is

wherein, $Y^5$ is H, halogen, lower alkyl, or lower haloalkyl.

In one embodiment of Formula II', $Y^2$ is hydroxymethyl, $Y^1$ is methyl, X is N, n is 0 and m is 0, and $Y^4$ is

wherein, $Y^5$ is H, halogen, lower alkyl, or lower haloalkyl.

In one embodiment of Formula II', $Y^2$ is hydroxymethyl, $Y^1$ is methyl, X is N, n is 0 and m is 0, and $Y^4$ is

wherein, $Y^5$ is H, halogen, lower alkyl, or lower haloalkyl.

In one embodiment of Formula II', $Y^4$ is lower alkyl.

In one embodiment of Formula II', $Y^2$ is hydroxymethyl, $Y^1$ is methyl, X is CH, n is 0 and m is 0, and $Y^4$ is lower alkyl.

In one variation of the above embodiment of Formula II'
R is —$R^1$—$R^2$—$R^3$;
$R^1$ is phenyl or pyridyl,
$R^2$ is —C(=O);
$R^3$ is $R^4$; and
$R^4$ is morpholine or piperazine, optionally substituted with one or more lower alkyl.

In another variation of the above embodiment of Formula II',
R is —$R^2$—$R^3$;
$R^2$ is —C(=O)NH;
$R^3$ is H or $R^4$; and
$R^4$ is lower alkyl.

In yet another variation of the above embodiment of Formula II',
R is $R^1$; and
$R^1$ is pyrazolyl, optionally substituted with $R^{1'}$.

In one embodiment of Formula II', $Y^2$ is hydroxymethyl, $Y^1$ is methyl, X is N, n is 0 and m is 0, and $Y^4$ is lower alkyl.

In one embodiment of Formula II', $Y^4$ is

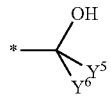

wherein, $Y^5$ and $Y^6$ are independently H, lower alkyl, or lower haloalkyl.

In one embodiment of Formula II', $Y^2$ is hydroxymethyl, $Y^1$ is methyl, X is CH, n is 0 and m is 0, and $Y^4$ is

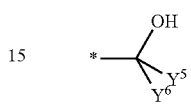

wherein, $Y^5$ and $Y^6$ are independently H, lower alkyl, or lower haloalkyl.

In one variation of the above embodiment of Formula II',
R is —$R^1$—$R^2$—$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

In another variation of the above embodiment of Formula II',
R is —$R^2$—$R^3$;
$R^2$ is —C(=O)NH;
$R^3$ is H or $R^4$; and
$R^4$ is lower alkyl.

In yet another variation of the above embodiment of Formula II',
R is $R^1$; and
$R^1$ is pyrazolyl, optionally substituted with $R^{1'}$.

In one embodiment of Formula II', $Y^2$ is hydroxymethyl, $Y^1$ is methyl, X is CH, n is 0 and m is 0, and $Y^4$ is

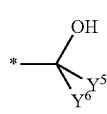

wherein, $Y^5$ and $Y^6$ are independently H, lower alkyl, or lower haloalkyl.

In one embodiment of Formula II', $Y^2$ is hydroxymethyl, $Y^1$ is methyl, X is N, n is 0 and m is 0, and $Y^4$ is

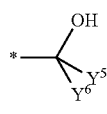

wherein, $Y^5$ and $Y^6$ are independently H, lower alkyl, or lower haloalkyl.

In one embodiment of Formula II', $Y^2$ is hydroxymethyl, $Y^1$ is methyl, X is N, n is 0 and m is 0, and $Y^4$ is

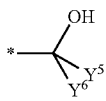

wherein, $Y^5$ and $Y^6$ are independently H, lower alkyl, or lower haloalkyl.

In one embodiment of Formula II', $Y^4$ is

wherein, $Y^5$ and $Y^6$ are independently H or lower alkyl.

In one embodiment of Formula II', $Y^2$ is hydroxymethyl, $Y^1$ is methyl, X is CH, n is 0 and m is 0, and $Y^4$ is

wherein, $Y^5$ and $Y^6$ are independently H or lower alkyl.

In one variation of the above embodiment of Formula II',
R is —$R^1$—$R^2$—$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

In another variation of the above embodiment of Formula II',
R is —$R^2$—$R^3$;
$R^2$ is —C(=O)NH;
$R^3$ is H or $R^4$; and
$R^4$ is lower alkyl.

In yet another variation of the above embodiment of Formula II',
R is $R^1$; and
$R^1$ is pyrazolyl, optionally substituted with $R^{1'}$.

In one embodiment of Formula II', $Y^2$ is hydroxymethyl, $Y^1$ is methyl, X is CH, n is 0 and m is 0, and $Y^4$ is

wherein, $Y^5$ and $Y^6$ are independently H or lower alkyl.

In one embodiment of Formula II', $Y^2$ is hydroxymethyl, $Y^1$ is methyl, X is N, n is 0 and m is 0, and $Y^4$ is

wherein, $Y^5$ and $Y^6$ are independently H or lower alkyl.

In one embodiment of Formula II', $Y^2$ is hydroxymethyl, $Y^1$ is methyl, X is N, n is 0 and m is 0, and $Y^4$ is

wherein, $Y^5$ and $Y^6$ are independently H or lower alkyl.

In one embodiment of Formula II', $Y^4$ is

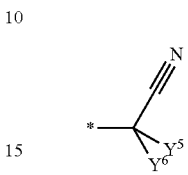

wherein, $Y^5$ and $Y^6$ are independently lower alkyl, or lower haloalkyl.

In one embodiment of Formula II', $Y^1$ is methyl, X is CH, n is 0 and m is 0, and $Y^4$ is

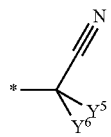

wherein, $Y^5$ and $Y^6$ are independently H, lower alkyl, or lower haloalkyl.

In one variation of the above embodiment of Formula II',
R is —$R^1$—$R^2$—$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

In another variation of the above embodiment of Formula II',
R is —$R^2$—$R^3$;
$R^2$ is —C(=O)NH;
$R^3$ is H or $R^4$; and
$R^4$ is lower alkyl.

In yet another variation of the above embodiment of Formula II',
R is $R^1$; and
$R^1$ is pyrazolyl, optionally substituted with $R^{1'}$.

In one embodiment of Formula II', $Y^1$ is methyl, X is CH, n is 0 and m is 0, and $Y^4$ is

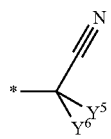

wherein, $Y^5$ and $Y^6$ are independently H, lower alkyl, or lower haloalkyl.

In one embodiment of Formula II', $Y^1$ is methyl, X is N, n is 0 and m is 0, and $Y^4$ is

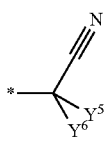

wherein, $Y^5$ and $Y^6$ are independently H, lower alkyl, or lower haloalkyl.

In one embodiment of Formula II', $Y^1$ is methyl, X is N, n is 0 and m is 0, and $Y^4$ is

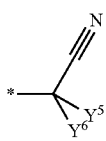

wherein, $Y^5$ and $Y^6$ are independently H, lower alkyl, or lower haloalkyl.

The application provides a compound of Formula III',

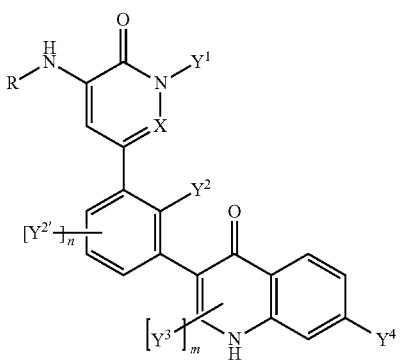

III' wherein:
R is H, —$R^1$, —$R^1$—$R^2$—$R^3$, —$R^1$—$R^3$, or —$R^2$—$R^3$;
  $R^1$ is aryl, heteroaryl, cycloalkyl, or heterocycloalkyl, and is optionally substituted with $R^{1'}$;
    $R^{1'}$ is lower alkyl, hydroxy, lower hydroxyalkyl, lower alkoxy, halogen, nitro, amino, cycloalkyl, heterocycloalkyl, cyano, or lower haloalkyl;
  $R^2$ is —C(=O), —C(=O)O, —C(=O)N($R^{2'}$), —(CH$_2$)$_q$, or —S(=O)$_2$;
    $R^{2'}$ is H or lower alkyl;
    q is 1, 2, or 3;
  $R^3$ is H or $R^4$;
    $R^4$ is lower alkyl, lower alkoxy, lower heteroalkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with one or more lower alkyl, hydroxy, oxo, lower hydroxyalkyl, lower alkoxy, halogen, nitro, amino, cyano, lower alkylsulfonyl, or lower haloalkyl;
X is CH or N;
$Y^1$ is H or lower alkyl;
$Y^2$ is $Y^{2a}$ or $Y^{2b}$;
  $Y^{2a}$ is H or halogen;
  $Y^{2b}$ is lower alkyl, optionally substituted with one or more $Y^{2b'}$;

$Y^{2b'}$ is hydroxy, lower alkoxy, or halogen;
each $Y^{2'}$ is independently $Y^{2'a}$ or $Y^{2'b}$;
  $Y^{2'a}$ is halogen;
  $Y^{2'b}$ is lower alkyl, optionally substituted with one or more $Y^{2'b'}$);
  $Y^{2'b'}$ is hydroxy, lower alkoxy, or halogen;
n is 0, 1, 2, or 3.
$Y^3$ is H, halogen, or lower alkyl, wherein lower alkyl is optionally substituted with one or more substituents selected from the group consisting of hydroxy, lower alkoxy, amino, and halogen;
m is 0 or 1;
$Y^4$ is $Y^{4a}$, $Y^{4b}$, $Y^{4c}$, $Y^{4d}$;
  $Y^{4a}$ is H or halogen;
  $Y^{4b}$ is lower alkyl, optionally substituted with one or more substituents selected from the group consisting of haloalkyl, halogen, hydroxy, amino, and lower alkoxy;
  $Y^{4c}$ is lower cycloalkyl, optionally substituted with one or more substituents selected from the group consisting of lower alkyl, lower haloalkyl, halogen, hydroxy, amino, and lower alkoxy; and
  $Y^{4d}$ is amino, optionally substituted with one or more lower alkyl;
or a pharmaceutically acceptable salt thereof.

In one embodiment of Formula III', $Y^1$ is methyl.
In one embodiment of Formula III', n is 0 and m is 0.
In one embodiment of Formula III', $Y^2$ is hydroxymethyl.
In one embodiment of Formula III', $Y^1$ is methyl, n is 0 and m is 0.
In one embodiment of Formula III', $Y^2$ is hydroxymethyl, $Y^1$ is methyl, n is 0 and m is 0.
In one embodiment of Formula III', X is N.
In one embodiment of Formula III', $Y^1$ is methyl, n is 0, m is 0, and X is N.
In one embodiment of Formula III', $Y^2$ is hydroxymethyl, $Y^1$ is methyl, n is 0, m is 0, and X is N.
In one embodiment of Formula III', $Y^1$ is methyl, n is 0, m is 0, and X is CH.
In one embodiment of Formula III', $Y^2$ is hydroxymethyl, $Y^1$ is methyl, n is 0, m is 0, and X is CH.
In one embodiment of Formula III', X is CH.
In one embodiment of Formula III', $Y^2$ is methyl.
In one embodiment of Formula III', $Y^2$ is hydroxyethyl.
In one embodiment of Formula III', $Y^2$ is halogen.
In one embodiment of Formula III', $Y^4$ is

wherein, $Y^5$ is H, halogen, lower alkyl, or lower haloalkyl.
In one embodiment of Formula III', $Y^2$ is hydroxymethyl, $Y^1$ is methyl, n is 0, m is 0, X is CH, and $Y^4$ is

wherein, $Y^5$ is H, halogen, lower alkyl, or lower haloalkyl.
In one variation of the above embodiment of Formula III',
R is —$R^1$—$R^2$—$R^3$;
$R^1$ is phenyl or pyridyl;
$R^2$ is —C(=O);
$R^3$ is $R^4$; and $R^4$ is morpholine or piperazine, optionally substituted with one or more lower alkyl.

In another variation of the above embodiment of Formula III',
R is —$R^2$—$R^3$;
$R^2$ is —C(=O)NH;
$R^3$ is H or $R^4$; and
$R^4$ is lower alkyl.

In yet another variation of the above embodiment of Formula III',
R is $R^1$; and
$R^1$ is pyrazolyl, optionally substituted with $R^{1'}$.

In one embodiment of Formula III', $Y^2$ is hydroxymethyl, $Y^1$ is methyl, n is 0, m is 0, and X is N, and $Y^4$ is

wherein, $Y^5$ is H, halogen, lower alkyl, or lower haloalkyl.

In one embodiment of Formula III', $Y^4$ is

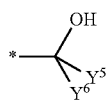

wherein, $Y^5$ and $Y^6$ are independently H, lower alkyl, or lower haloalkyl.

In one embodiment of Formula III', $Y^2$ is hydroxymethyl, $Y^1$ is methyl, n is 0, m is 0, X is CH, and $Y^4$ is

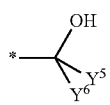

wherein, $Y^5$ and $Y^6$ are independently H, lower alkyl, or lower haloalkyl.

In one variation of the above embodiment of Formula III',
R is —$R^1$—$R^2$—$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

In another variation of the above embodiment of Formula III',
R is —$R^2$—$R^3$;
$R^2$ is —C(=O)NH;
$R^3$ is H or $R^4$; and
$R^4$ is lower alkyl.

In yet another variation of the above embodiment of Formula III',
R is $R^1$; and
$R^1$ is pyrazolyl, optionally substituted with $R^{1'}$.

In one embodiment of Formula III', $Y^2$ is hydroxymethyl, $Y^1$ is methyl, n is 0, m is 0, and X is N, and $Y^4$ is

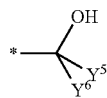

wherein, $Y^5$ and $Y^6$ are independently H, lower alkyl, or lower haloalkyl.

In one embodiment of Formula III', $Y^4$ is

wherein, $Y^5$ and $Y^6$ are independently H or lower alkyl.

In one embodiment of Formula III', $Y^2$ is hydroxymethyl, $Y^1$ is methyl, n is 0, m is 0, X is CH, and $Y^4$ is

wherein, $Y^5$ and $Y^6$ are independently H or lower alkyl.

In one variation of the above embodiment of Formula III',
R is —$R^1$—$R^2$—$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

In another variation of the above embodiment of Formula III',
R is —$R^2$—$R^3$;
$R^2$ is —C(=O)NH;
$R^3$ is H or $R^4$; and
$R^4$ is lower alkyl.

In yet another variation of the above embodiment of Formula III',
R is $R^1$; and
$R^1$ is pyrazolyl, optionally substituted with $R^{1'}$.

In one embodiment of Formula III', $Y^2$ is hydroxymethyl, $Y^1$ is methyl, n is 0, m is 0, and X is N, and $Y^4$ is

wherein, $Y^5$ and $Y^6$ are independently H or lower alkyl.

In one embodiment of Formula III', $Y^4$ is

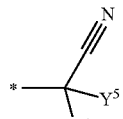

wherein, $Y^5$ and $Y^6$ are independently H, lower alkyl, or lower haloalkyl.

In one embodiment of Formula III', $Y^2$ is hydroxymethyl, $Y^1$ is methyl, n is 0, m is 0, X is CH, and $Y^4$ is

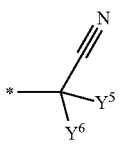

wherein, $Y^5$ and $Y^6$ are independently H, lower alkyl, or lower haloalkyl.

In one variation of the above embodiment of Formula III',
R is —$R^1$—$R^2$—$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

In another variation of the above embodiment of Formula III',
R is —$R^2$—$R^3$;
$R^2$ is —C(=O)NH;
$R^3$ is H or $R^4$; and
$R^4$ is lower alkyl.

In yet another variation of the above embodiment of Formula III',
R is $R^1$, and
$R^1$ is pyrazolyl, optionally substituted with $R^{1'}$.

In one embodiment of Formula III', $Y^2$ is hydroxymethyl, $Y^1$ is methyl, n is 0, m is 0, and X is N, and $Y^4$ is

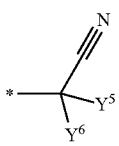

wherein, $Y^5$ and $Y^6$ are independently H, lower alkyl, or lower haloalkyl.

The application provides a compound of Formula IV',

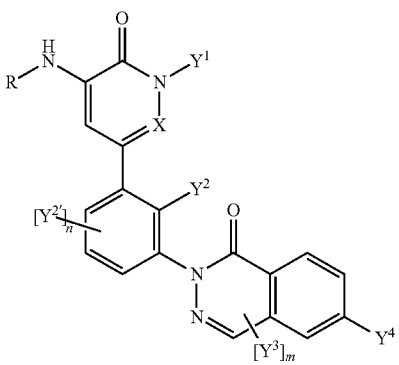

wherein:
R is H, —$R^1$, —$R^1$—$R^2$—$R^3$, —$R^1$—$R^3$, or —$R^2$—$R^3$;
  $R^1$ is aryl, heteroaryl, cycloalkyl, or heterocycloalkyl, and is optionally substituted with $R^{1'}$;
    $R^{1'}$ is lower alkyl, hydroxy, lower hydroxyalkyl, lower alkoxy, halogen, nitro, amino, cycloalkyl, heterocycloalkyl, cyano, or lower haloalkyl;
  $R^2$ is —C(=O), —C(=O)O, —C(=O)N($R^{2'}$), —$(CH_2)_q$, or —S(=O)$_2$;
    $R^{2'}$ is H or lower alkyl;
    q is 1, 2, or 3;
  $R^3$ is H or $R^4$;
  $R^4$ is lower alkyl, lower alkoxy, lower heteroalkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with one or more lower alkyl, hydroxy, oxo, lower hydroxyalkyl, lower alkoxy, halogen, nitro, amino, cyano, lower alkylsulfonyl, or lower haloalkyl;
X is CH or N;
$Y^1$ is H or lower alkyl;
$Y^2$ is $Y^{2a}$ or $Y^{2b}$;
  $Y^{2a}$ is H or halogen;
  $Y^{2b}$ is lower alkyl, optionally substituted with one or more $Y^{2b'}$;
    $Y^{2b'}$ is hydroxy, lower alkoxy, or halogen;
each $Y^{2'}$ is independently $Y^{2'a}$ or $Y^{2'b}$;
  $Y^{2'a}$ is halogen;
  $Y^{2'b}$ is lower alkyl, optionally substituted with one or more $Y^{2'b'}$;
    $Y^{2'b'}$ is hydroxy, lower alkoxy, or halogen;
n is 0, 1, 2, or 3.
$Y^3$ is H, halogen, or lower alkyl, wherein lower alkyl is optionally substituted with one or more substituents selected from the group consisting of hydroxy, lower alkoxy, amino, and halogen;
m is 0 or 1;
$Y^4$ is $Y^{4a}$, $Y^{4b}$, $Y^{4c}$, or $Y^{4d}$;
  $Y^{4a}$ is H or halogen;
  $Y^{4b}$ is lower alkyl, optionally substituted with one or more substituents selected from the group consisting of haloalkyl, halogen, hydroxy, amino, and lower alkoxy;
  $Y^{4c}$ is lower cycloalkyl, optionally substituted with one or more substituents selected from the group consisting of lower alkyl, lower haloalkyl, halogen, hydroxy, amino, and lower alkoxy; and
  $Y^{4d}$ is amino, optionally substituted with one or more lower alkyl;
or a pharmaceutically acceptable salt thereof.

In one embodiment of Formula IV', $Y^1$ is methyl.
In one embodiment of Formula IV', n is 0 and m is 0.
In one embodiment of Formula IV', $Y^2$ is hydroxymethyl.
In one embodiment of Formula IV', $Y^1$ is methyl, n is 0 and m is 0.
In one embodiment of Formula IV', $Y^2$ is hydroxymethyl, $Y^1$ is methyl, n is 0 and m is 0.
In one embodiment of Formula IV', X is N.
In one embodiment of Formula IV', $Y^1$ is methyl, n is 0, m is 0, and X is N.
In one embodiment of Formula IV', $Y^2$ is hydroxymethyl, $Y^1$ is methyl, n is 0, m is 0, and X is N.
In one embodiment of Formula IV', $Y^1$ is methyl, n is 0, m is 0, and X is CH.
In one embodiment of Formula IV', $Y^2$ is hydroxymethyl, $Y^1$ is methyl, n is 0, m is 0, and X is CH.
In one embodiment of Formula IV', X is CH.
In one embodiment of Formula IV', $Y^2$ is methyl.
In one embodiment of Formula IV', $Y^2$ is hydroxyethyl.
In one embodiment of Formula IV', $Y^2$ is halogen.
In one embodiment of Formula IV', $Y^4$ is

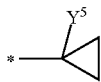

wherein, $Y^5$ is H, halogen, lower alkyl, or lower haloalkyl.

In one embodiment of Formula IV', $Y^2$ is hydroxymethyl, $Y^1$ is methyl, n is 0, m is 0, X is CH, and $Y^4$ is

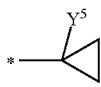

wherein, $Y^5$ is H, halogen, lower alkyl, or lower haloalkyl.

In one variation of the above embodiment of Formula IV', R is —$R^1$—$R^2$—$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

In another variation of the above embodiment of Formula IV',
R is —$R^2$—$R^3$;
$R^2$ is —C(=O)NH;
$R^3$ is H or $R^4$; and
$R^4$ is lower alkyl.

In yet another variation of the above embodiment of Formula IV',
R is $R^1$; and
$R^1$ is pyrazolyl, optionally substituted with $R^{1'}$.

In one embodiment of Formula IV', $Y^2$ is hydroxymethyl, $Y^1$ is methyl, n is 0, m is 0, and X is N, and $Y^4$ is

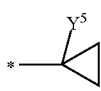

wherein, $Y^5$ is H, halogen, lower alkyl, or lower haloalkyl.

In one embodiment of Formula IV', $Y^4$ is

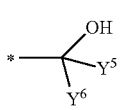

wherein, $Y^5$ and $Y^6$ are independently H, lower alkyl, or lower haloalkyl.

In one embodiment of Formula IV', $Y^2$ is hydroxymethyl, $Y^1$ is methyl, n is 0, m is 0, X is CH, and $Y^4$ is

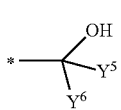

wherein, $Y^5$ and $Y^6$ are independently H, lower alkyl, or lower haloalkyl.

In one variation of the above embodiment of Formula IV',
R is —$R^1$—$R^2$—$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

In another variation of the above embodiment of Formula IV',
R is —$R^2$—$R^3$;
$R^2$ is —C(=O)NH;
$R^3$ is H or $R^4$; and
$R^4$ is lower alkyl.

In yet another variation of the above embodiment of Formula IV',
R is $R^1$; and
$R^1$ is pyrazolyl, optionally substituted with $R^{1'}$.

In one embodiment of Formula IV', $Y^2$ is hydroxymethyl, $Y^1$ is methyl, n is 0, m is 0, and X is N, and $Y^4$ is

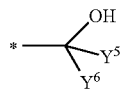

wherein, $Y^5$ and $Y^6$ are independently H, lower alkyl, or lower haloalkyl.

In one embodiment of Formula IV', $Y^4$ is

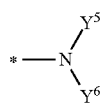

wherein, $Y^5$ and $Y^6$ are independently H or lower alkyl.

In one embodiment of Formula IV', $Y^2$ is hydroxymethyl, $Y^1$ is methyl, n is 0, m is 0, X is CH, and $Y^4$ is

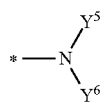

wherein, $Y^5$ and $Y^6$ are independently H or lower alkyl.

In one variation of the above embodiment of Formula IV',
R is —$R^1$—$R^2$—$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

In another variation of the above embodiment of Formula IV',
R is —$R^2$—$R^3$;
$R^2$ is —C(=O)NH;
$R^3$ is H or $R^4$; and
$R^4$ is lower alkyl.

In yet another variation of the above embodiment of Formula IV',
R is $R^1$; and
$R^1$ is pyrazolyl, optionally substituted with $R^{1'}$.

In one embodiment of Formula IV', $Y^2$ is hydroxymethyl, $Y^1$ is methyl, n is 0, m is 0, and X is N, and $Y^4$ is

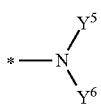

wherein, $Y^5$ and $Y^6$ are independently H or lower alkyl.

In one embodiment of Formula IV', $Y^4$ is

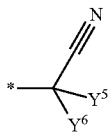

wherein, $Y^5$ and $Y^6$ are independently H, lower alkyl, or lower haloalkyl.

In one embodiment of Formula IV', $Y^2$ is hydroxymethyl, $Y^1$ is methyl, n is 0, m is 0, X is CH, and $Y^4$ is

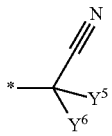

wherein, $Y^5$ and $Y^6$ are independently H, lower alkyl, or lower haloalkyl.

In one variation of the above embodiment of Formula IV',
R is —$R^1$—$R^2$—$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

In another variation of the above embodiment of Formula IV',
R is —$R^2$—$R^3$;
$R^2$ is —C(=O)NH;
$R^3$ is H or $R^4$; and
$R^4$ is lower alkyl.

In yet another variation of the above embodiment of Formula IV',
R is $R^1$; and
$R^1$ is pyrazolyl, optionally substituted with $R^{1'}$.

In one embodiment of Formula IV', $Y^2$ is hydroxymethyl, $Y^1$ is methyl, n is 0, m is 0, and X is N, and $Y^4$ is

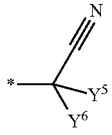

wherein, $Y^5$ and $Y^6$ are independently H, lower alkyl, or lower haloalkyl.

The application provides a compound of Formula V',

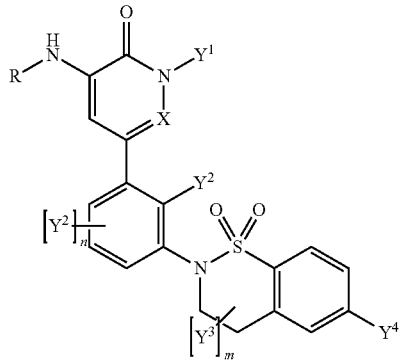

wherein:
R is H, —$R^1$, —$R^1$—$R^2$—$R^3$, —$R^1$—$R^3$, or —$R^2$—$R^3$;
   $R^1$ is aryl, heteroaryl, cycloalkyl, or heterocycloalkyl, and is optionally substituted with $R^{1'}$;
   $R^{1'}$ is lower alkyl, hydroxy, lower hydroxyalkyl, lower alkoxy, halogen, nitro, amino, cycloalkyl, heterocycloalkyl, cyano, or lower haloalkyl;
   $R^2$ is —C(=O), —C(=O)O, —C(=O)N($R^{2'}$), —(CH$_2$)$_q$, or —S(=O)$_2$;
   $R^{2'}$ is H or lower alkyl;
   q is 1, 2, or 3;
   $R^3$ is H or $R^4$;
   $R^4$ is lower alkyl, lower alkoxy, lower heteroalkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with one or more lower alkyl, hydroxy, oxo, lower hydroxyalkyl, lower alkoxy, halogen, nitro, amino, cyano, lower alkylsulfonyl, or lower haloalkyl;
X is CH or N;
$Y^1$ is H or lower alkyl;
$Y^2$ is $Y^{2a}$ or $Y^{2b}$;
   $Y^{2a}$ is H or halogen;
   $Y^{2b}$ is lower alkyl, optionally substituted with one or more $Y^{2b'}$;
   $Y^{2b'}$ is hydroxy, lower alkoxy, or halogen;
each $Y^{2'}$ is independently $Y^{2'a}$ or $Y^{2'b}$;
   $Y^{2'a}$ is halogen;
   $Y^{2'b}$ is lower alkyl, optionally substituted with one or more $Y^{2'b'}$;
   $Y^{2'b'}$ is hydroxy, lower alkoxy, or halogen;
n is 0, 1, 2, or 3.
$Y^3$ is H, halogen, or lower alkyl, wherein lower alkyl is optionally substituted with one or more substituents selected from the group consisting of hydroxy, lower alkoxy, amino, and halogen;
m is 0 or 1;
$Y^4$ is $Y^{4a}$, $Y^{4b}$, $Y^{4c}$, or $Y^{4d}$;
   $Y^{4a}$ is H or halogen;
   $Y^{4b}$ is lower alkyl, optionally substituted with one or more substituents selected from the group consisting of lower haloalkyl, halogen, hydroxy, amino, and lower alkoxy;
   $Y^{4c}$ is lower cycloalkyl, optionally substituted with one or more substituents selected from the group consisting of lower alkyl, lower haloalkyl, halogen, hydroxy, amino, and lower alkoxy; and
   $Y^{4d}$ is amino, optionally substituted with one or more lower alkyl;
or a pharmaceutically acceptable salt thereof.

In one embodiment of Formula V', Y$^1$ is methyl.
In one embodiment of Formula V', Y$^2$ is hydroxymethyl.
In one embodiment of Formula V', X is N.
In one embodiment of Formula V', X is N, n is 0 and m is 0.
In one embodiment of Formula V', Y$^2$ is hydroxymethyl, X is N, n is 0 and m is 0.
In one embodiment of Formula V', Y$^1$ is methyl, X is N, n is 0 and m is 0.
In one embodiment of Formula V', Y$^2$ is hydroxymethyl, Y$^1$ is methyl, X is N, n is 0 and m is 0.
In one embodiment of Formula V', Y$^2$ is methyl.
In one embodiment of Formula V', Y$^2$ is hydroxyethyl.
In one embodiment of Formula V', Y$^2$ is halogen.
In one embodiment of Formula V', X is CH.
In one embodiment of Formula V', X is CH, n is 0 and m is 0.
In one embodiment of Formula V', Y$^2$ is hydroxymethyl, X is CH, n is 0 and m is 0.
In one embodiment of Formula V', Y$^1$ is methyl, X is CH, n is 0 and m is 0.
In one embodiment of Formula V', Y$^2$ is hydroxymethyl, Y$^1$ is methyl, X is CH, n is 0 and m is 0.
In one embodiment of Formula V', Y$^4$ is

wherein, Y$^5$ is H, halogen, lower alkyl, or lower haloalkyl.
In one embodiment of Formula V', Y$^2$ is hydroxymethyl, Y$^1$ is methyl, X is CH, n is 0 and m is 0, and Y$^4$ is

wherein, Y$^5$ is H, halogen, lower alkyl, or lower haloalkyl.
In one variation of the above embodiment of Formula V'
R is —R$^1$—R$^2$—R$^3$;
R$^1$ is phenyl or pyridyl;
R$^2$ is —C(=O);
R$^3$ is R$^4$; and
R$^4$ is morpholine or piperazine, optionally substituted with one or more lower alkyl.
In another variation of the above embodiment of Formula V',
R is —R$^2$—R$^3$;
R$^2$ is —C(=O)NH;
R$^3$ is H or R$^4$; and
R$^4$ is lower alkyl.
In yet another variation of the above embodiment of Formula V',
R is R$^1$; and
R$^1$ is pyrazolyl, optionally substituted with R$^{1'}$.
In one embodiment of Formula V', Y$^2$ is hydroxymethyl, Y$^1$ is methyl, X is N, n is 0 and m is 0, and Y$^4$ is

wherein, Y$^5$ is H, halogen, lower alkyl, or lower haloalkyl.
In one embodiment of Formula V', Y$^4$ is lower alkyl.

In one embodiment of Formula V', Y$^2$ is hydroxymethyl, Y$^1$ is methyl, X is CH, n is 0 and m is 0, and Y$^4$ is lower alkyl.
In one variation of the above embodiment of Formula V'
R is —R$^1$—R$^2$—R$^3$;
R$^1$ is phenyl or pyridyl;
R$^2$ is —C(=O);
R$^3$ is R$^4$; and
R$^4$ is morpholine or piperazine, optionally substituted with one or more lower alkyl.
In another variation of the above embodiment of Formula V',
R is —R$^2$—R$^3$;
R$^2$ is —C(=O)NH;
R$^3$ is H or R$^4$; and
R$^4$ is lower alkyl.
In yet another variation of the above embodiment of Formula V',
R is R$^1$; and
R$^1$ is pyrazolyl, optionally substituted with R$^{1'}$.
In one embodiment of Formula V', Y$^2$ is hydroxymethyl, Y$^1$ is methyl, X is N, n is 0 and m is 0, and Y$^4$ is lower alkyl.
In one embodiment of Formula V', Y$^4$ is

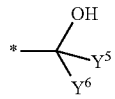

wherein, Y$^5$ and Y$^6$ are independently H, lower alkyl, or lower haloalkyl.
In one embodiment of Formula V', Y$^2$ is hydroxymethyl, Y$^1$ is methyl, X is CH, n is 0 and m is 0, and Y$^4$ is

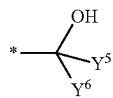

wherein, Y$^5$ and Y$^6$ are independently H, lower alkyl, or lower haloalkyl.
In one variation of the above embodiment of Formula V',
R is —R$^1$—R$^2$—R$^3$;
R$^1$ is phenyl or pyridyl;
R$^2$ is —C(=O);
R$^3$ is R$^4$; and
R$^4$ is morpholine or piperazine, optionally substituted with one or more lower alkyl.
In another variation of the above embodiment of Formula V',
R is —R$^2$—R$^3$;
R$^2$ is —C(=O)NH;
R$^3$ is H or R$^4$; and
R$^4$ is lower alkyl.
In yet another variation of the above embodiment of Formula V',
R is R$^1$; and
R$^1$ is pyrazolyl, optionally substituted with R$^{1'}$.

In one embodiment of Formula V', $Y^2$ is hydroxymethyl, $Y^1$ is methyl, X is N, n is 0 and m is 0, and $Y^4$ is

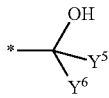

wherein, $Y^5$ and $Y^6$ are independently H, lower alkyl, or lower haloalkyl.

In one embodiment of Formula V', $Y^4$ is

wherein, $Y^5$ and $Y^6$ are independently H or lower alkyl.

In one embodiment of Formula V', $Y^2$ is hydroxymethyl, $Y^1$ is methyl, X is CH, n is 0 and m is 0, and $Y^4$ is

wherein, $Y^5$ and $Y^6$ are independently H or lower alkyl.

In one variation of the above embodiment of Formula V',
R is —$R^1$—$R^2$—$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

In another variation of the above embodiment of Formula V',
R is —$R^2$—$R^3$;
$R^2$ is —C(=O)NH;
$R^3$ is H or $R^4$; and
$R^4$ is lower alkyl.

In yet another variation of the above embodiment of Formula V',
R is $R^1$; and
$R^1$ is pyrazolyl, optionally substituted with $R^{1'}$.

In one embodiment of Formula V', $Y^2$ is hydroxymethyl, $Y^1$ is methyl, X is N, n is 0 and m is 0, and $Y^4$ is

wherein, $Y^5$ and $Y^6$ are independently H or lower alkyl.

In one embodiment of Formula V', $Y^4$ is

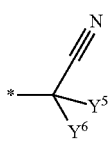

wherein, $Y^5$ and $Y^6$ are independently H, lower alkyl, or lower haloalkyl.

In one embodiment of Formula V', $Y^1$ is methyl, X is CH, n is 0 and m is 0, and $Y^4$ is

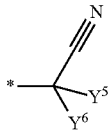

wherein, $Y^5$ and $Y^6$ are independently H, lower alkyl, or lower haloalkyl.

In one variation of the above embodiment of Formula V',
R is —$R^1$—$R^2$—$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

In another variation of the above embodiment of Formula V',
R is —$R^2$—$R^3$;
$R^2$ is —C(=O)NH;
$R^3$ is H or $R^4$; and
$R^4$ is lower alkyl.

In yet another variation of the above embodiment of Formula V',
R is $R^1$; and
$R^1$ is pyrazolyl, optionally substituted with $R^{1'}$.

In one embodiment of Formula V', $Y^1$ is methyl, X is N, n is 0 and m is 0, and $Y^4$ is

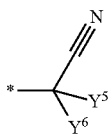

wherein, $Y^5$ and $Y^6$ are independently H, lower alkyl, or lower haloalkyl.

The application provides a method for treating an inflammatory and/or autoimmune condition comprising administering to a patient in need thereof a therapeutically effective amount of the Btk inhibitor compound of any one of the above Formulae or variations thereof.

The application provides a method for treating arthritis comprising administering to a patient in need thereof a therapeutically effective amount of the Btk inhibitor compound of any one of the above Formulae or variations thereof.

The application provides a method of inhibiting B-cell proliferation comprising administering to a patient in need thereof a therapeutically effective amount of the Btk inhibitor compound of any one of the above Formulae or variations thereof.

The application provides a method for inhibiting Btk activity comprising administering the Btk inhibitor compound of any one of the above Formulae or variations thereof, wherein the Btk inhibitor compound exhibits an $IC_{50}$ of 50 micromolar or less in an in vitro biochemical assay of Btk activity.

In one variation of the above method, the Btk inhibitor compound exhibits an $IC_{50}$ of 100 nanomolar or less in an in vitro biochemical assay of Btk activity.

In one variation of the above method, the compound exhibits an $IC_{50}$ of 10 nanomolar or less in an in vitro biochemical assay of Btk activity.

The application provides a method for treating an inflammatory condition comprising co-administering to a patient in need thereof a therapeutically effective amount of an anti-inflammatory compound in combination with the Btk inhibitor compound of any one of the above Formulae or variations thereof.

The application provides a method for treating arthritis comprising co-administering to a patient in need thereof a therapeutically effective amount of an anti-inflammatory compound in combination with the Btk inhibitor compound of any one of the above Formulae or variations thereof.

The application provides a method for treating a lymphoma or a BCR-ABL1+ leukemia cells by administering to a patient in need thereof a therapeutically effective amount of the Btk inhibitor compound of any one of the above Formulae or variations thereof.

The application provides a pharmaceutical composition comprising the Btk inhibitor compound of any one of the above Formulae or variations thereof, admixed with at least one pharmaceutically acceptable carrier, excipient or diluent.

DETAILED DESCRIPTION OF THE INVENTION

The present application provides compounds of generic Formulae I-IV, which comprise the Btk inhibitor compounds of Formulae I-1 to I-3, II-1 to II-4, III-1 to III-14, and IV-1 to IV-4, wherein variables Q, R, X, $Y^1$, $Y^2$, $Y^3$, $Y^4$, n, and m are as defined herein above.

In one embodiment of the present invention, there is provided a compound according to generic Formula I which comprises the exemplified Btk inhibitor compounds of Formulae I-1 to I-3. In another embodiment of the present invention, there is provided a compound according to generic Formula II which comprises the exemplified Btk inhibitor compounds of Formulae II-1 to II-4. In yet another embodiment of the present invention, there is provided a compound according to generic Formula III which comprises the exemplified Btk inhibitor compounds of Formulae III-1 to III-14. In yet another embodiment of the present invention, there is provided a compound according to generic Formula IV which comprises the exemplified Btk inhibitor compounds of Formulae IV-1 to IV-4.

The present application discloses 5-phenyl-1H-pyridin-2-one and 6-phenyl-2H-pyridazin-3-one derivatives according to generic Formulae I-IV:

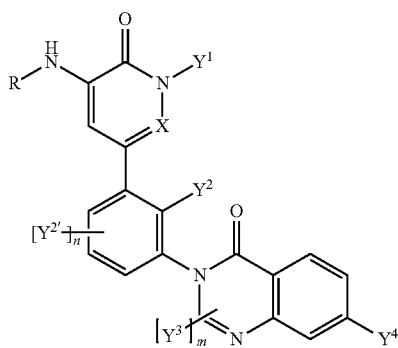

I

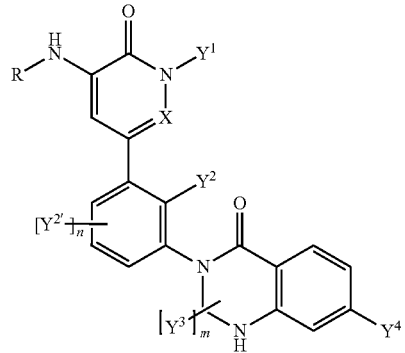

II

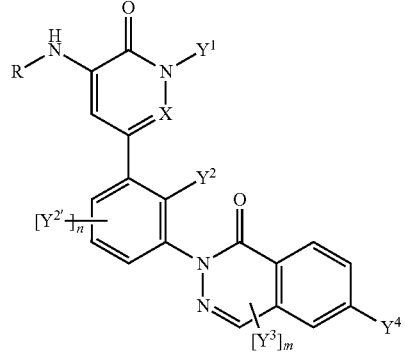

III

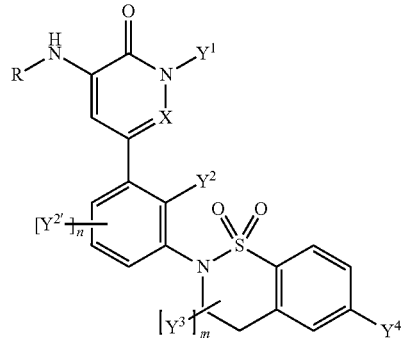

IV

The phrase "as defined herein above" refers to the broadest definition for each group as provided in the Summary of the Invention or the broadest claim. In all other aspects, variations and embodiments provided, substituents which can be present in each embodiment and which are not explicitly defined retain the broadest definition provided in the Summary of the Invention.

The compounds of generic Formulae I-IV inhibit Bruton's tyrosine kinase (Btk). Activation of Btk by upstream kinases results in activation of phospholipase-C☐ which, in turn, stimulates release of pro-inflammatory mediators. The compounds of generic Formulae I-IV, incorporating substituted side chains of 3,4-Dihydro-2H-isoquinolin-1-one, 2,3-Dihydro-1H-quinazolin-4-one, 2H-Isoquinolin-1-one, 3H-Quinazolin-4-one, 1H-Quinolin-4-one, 2H-Phthalazin-1-one, or 3,4-Dihydro-2H-benzo[e][1,2]thiazine 1,1-dioxide on the 5-phenyl-1H-pyridin-2-one and 6-phenyl-2H-pyridazin-3-one ring systems, exhibit unexpectedly enhanced inhibitory activity compared to analogues without said bicyclic side chains. Furthermore, inhibitory activity is enhanced when $Y^2$ is lower alkyl optionally substituted with hydroxy. Inhibitory activity is enhanced when $Y^2$ is hydroxymethyl.

Compounds of Formulae I-IV are useful in the treatment of arthritis and other anti-inflammatory and auto-immune diseases. Compounds according to Formulae I-IV are, accordingly, useful for the treatment of arthritis. Compounds of Formulae I-IV are useful for inhibiting Btk in cells and for modulating B-cell development. The present invention further comprises pharmaceutical compositions containing compounds of Formulae I-IV admixed with pharmaceutically acceptable carrier, excipients or diluents.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "-----"drawn through a bond each refer to the point of attachment of a functional group or other chemical moiety to the rest of the molecule of which it is a part. Thus, for example:

MeC(=O)OR⁴  wherein R⁴ =

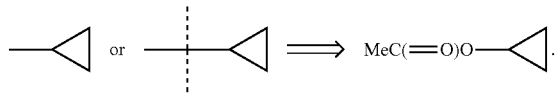

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds of formulae I-IV may exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10th Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "alkoxyalkyl" as used herein refers to the radical R'R"—, wherein R' is an alkoxy radical as defined herein, and R" is an alkylene radical as defined herein with the understanding that the attachment point of the alkoxyalkyl moiety will be on the alkylene radical. $C_{1-6}$ alkoxyalkyl denotes a group wherein the alkyl portion is comprised of 1-6 carbon atoms exclusive of carbon atoms in the alkoxy portion of the group. $C_{1-3}$ alkoxy-$C_{1-6}$ alkyl denotes a group wherein the alkyl portion is comprised of 1-6 carbon atoms and the alkoxy group is 1-3 carbons. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, t-butyloxybutyl, methoxypentyl, ethoxypentyl, propyloxypentyl including their isomers.

The term "hydroxyalkyl" as used herein denotes an alkyl radical as herein defined wherein one to three hydrogen atoms on different carbon atoms is/are replaced by hydroxyl groups.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, azulenyl, oxydiphenyl, biphenyl, methylenediphenyl, aminodiphenyl, diphenylsulfidyl, diphenylsulfonyl, diphenylisopropylidenyl, benzodioxanyl, benzodioxylyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like. The aryl group may optionally be fused to a cycloalkyl or heterocycloalkyl ring, as herein defined. Examples of an aryl group fused to a heterocycloalkyl group include 3,4-dihydro-1H-quinolin-2-one, 3,4-dihydro-2H-benzo[1,4]oxazine, and 1,2,3,4-tetrahydro-isoquinoline. Preferred aryl include optionally substituted phenyl and optionally substituted naphthyl.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, oxazol, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halogen, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole and benzisothiazole. Bicyclic moieties can be optionally substituted on either ring; however the point of attachment is on a ring containing a heteroatom.

The term "heterocycloalkyl", "heterocyclyl", or "heterocycle" as used herein denotes a monovalent saturated cyclic radical, consisting of one or more fused or spirocyclic rings, preferably one to two rings, of three to eight atoms per ring, incorporating one or more ring heteroatoms (chosen from N, O or $S(O)_{0-2}$), and which can optionally be independently substituted with one or more, preferably one or two substituents selected from hydroxy, oxo, cyano, lower alkyl, lower alkoxy, lower haloalkoxy, alkylthio, halogen, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (MAL or DIBAL-H), di-iso-propylethylamine (DIPEA), N,N-dimethyl acetamide (DMA), 4-N, N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), morn temperature (rt or RT), tert-butyldimethylsilyl or t-BuMe$_2$Si (TBDMS), triethylamine (TEA or Et$_3$N), 2,2,6,6-tetramethylpiperidine 1-oxyl (TEMPO), triflate or $CF_3SO_2$— (Tf), trifluoroacetic acid (TFA), 1,1'-bis-2,2,6,6-tetramethylheptane-2,6-dione (TMHD), O-benzotriazol-1-yl-N,N,N', N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA), Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

The term "arthritis" as used herein means acute rheumatic arthritis, chronic rheumatoid arthritis, chlamydial arthritis, chronic absorptive arthritis, chylous arthritis, arthritis based on bowel disease, filarial arthritis, gonorrheal arthritis, gouty arthritis, hemophilic arthritis, hypertrophic arthritis, juvenile chronic arthritis, Lyme arthritis, neonatal foal arthritis, nodular arthritis, ochronotic arthritis, psoriatic arthritis or suppurative arthritis, or the related diseases which require the administration to a mammal in a therapeutic effective dose of a compound of Formulae I-V in a sufficient dose to inhibit BTK.

The compounds of this invention can be used to treat subjects with autoimmune conditions or disorders. As used herein, the term "autoimmune condition" and like terms means a disease, disorder or condition caused by the immune system of an animal. Autoimmune disorders are those wherein the animal's own immune system mistakenly attacks itself, thereby targeting the cells, tissues, and/or organs of the animal's own body. For example, the autoimmune reaction is directed against the nervous system in multiple sclerosis and the gut in Crohn's disease. In other autoimmune disorders such as systemic lupus erythematosus (lupus), affected tissues and organs may vary among individuals with the same disease. One person with lupus may have affected skin and joints whereas another may have affected skin, kidney, and lungs. Ultimately, damage to certain tissues by the immune system may be permanent, as with destruction of insulin-producing cells of the pancreas in Type 1 diabetes mellitus. Specific autoimmune disorders that may be ameliorated using the compounds and methods of this invention include without limitation, autoimmune disorders of the nervous system (e.g., multiple sclerosis, myasthenia gravis, autoimmune neuropathies such as Guillain-Barre, and autoimmune uveitis), autoimmune disorders of the blood (e.g., autoimmune hemolytic anemia, pernicious anemia, and autoimmune thrombocytopenia), autoimmune disorders of the blood vessels (e.g., temporal arteritis, anti-phospholipid syndrome, vasculitides such as Wegener's granulomatosis, and Behcet's disease), autoimmune disorders of the skin (e.g., psoriasis, dermatitis herpetiformis, pemphigus vulgaris, and vitiligo), autoimmune disorders of the gastrointestinal system (e.g., Crohn's disease, ulcerative colitis, primary biliary cirrhosis, and autoimmune hepatitis), autoimmune disorders of the endocrine glands (e.g., Type 1 or immune-mediated diabetes mellitus, Grave's disease. Hashimoto's thyroiditis, autoimmune oophoritis and orchitis, and autoimmune disorder of the adrenal gland); and autoimmune disorders of multiple organs (including connective tissue and musculoskeletal system diseases) (e.g., rheumatoid arthritis, systemic lupus erythematosus, scleroderma, polymyositis, dermatomyositis, spondyloarthropathies such as ankylosing spondylitis, and Sjogren's syndrome) or the related diseases which require the administration to a mammal in a therapeutic effective dose of a compound of Formulae I-V in a sufficient dose to inhibit BTK. In addition, other immune system mediated diseases, such as graft-versus-host disease and allergic disorders, are also included in the definition of immune disorders herein. Because a number of immune disorders are caused by inflammation, there is some overlap between disorders that are considered immune disorders and inflammatory disorders. For the purpose of this invention, in the case of such an overlapping disorder, it may be considered either an immune disorder or an inflammatory disorder. "Treatment of an immune disorder" herein refers to administering a compound or a composition of the invention to a subject, who has an immune disorder, a symptom of such a disease or a predisposition towards such a disease, with the purpose to cure, relieve, alter, affect, or prevent the autoimmune disorder, the symptom of it, or the predisposition towards it.

As used herein, the term "asthma" means a pulmonary disease, disorder or condition characterized by reversible airway obstruction, airway inflammation, and increased airway responsiveness to a variety of stimuli.

The terms "treat," "treatment," or "treating" refer to both therapeutic treatment and prophylactic or preventative measures, wherein the object is to prevent or slow down (lessen) an undesired physiological change or disorder, such as the development or spread of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. For example, treating an inflammatory condition means reducing the extent or severity of the inflammation. The reduction can mean but is not limited to the complete ablation of inflammation. For example, the reduction can comprise a 5%, 10%, 20%, 30%, 40%, 50%, 60%, 70%, 80%, 90%, or 100% reduction, or any point in between, compared to an untreated or control subject as determined by any suitable measurement technique or assay disclosed herein or known in the art.

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of pyridinone and pyridazinone compounds of generic Formulae I-IV:

TABLE I

| Compound # | Structure | Nomenclature | MP |
|---|---|---|---|
| I-1 | 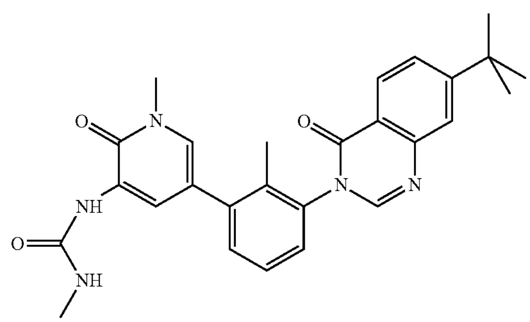 | 1-{5-[3-(7-tert-Butyl-4-oxo-4H-quinazolin-3-yl)-2-methyl-phenyl]-1-methyl-2-oxo-1,2-dihydro-pyridin-3-yl}-3-methyl-urea | |
| I-2 | 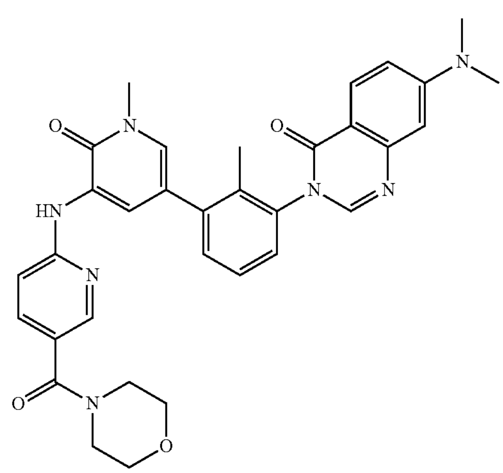 | 7-Dimethylamino-3-(2-methyl-3-{1-methyl-5-[5-(morpholine-4-carbonyl)-pyridin-2-ylamino]-6-oxo-1,6-dihydro-pyridin-3-yl}-phenyl)-3H-quinazolin-4-one | |

TABLE I-continued

| Compound # | Structure | Nomenclature | MP |
|---|---|---|---|
| I-3 | 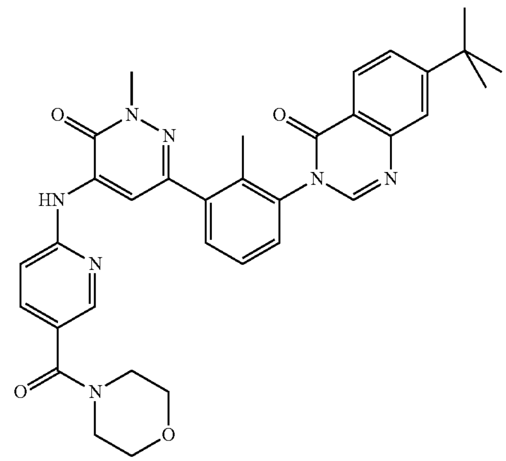 | 7-tert-Butyl-3-(2-methyl-3-{1-methyl-5-[5-(morpholine-4-carbonyl)-pyridin-2-ylamino]-6-oxo-1,6-dihydro-pyridazin-3-yl}-phenyl)-3H-quinazolin-4-one | |
| II-1 | 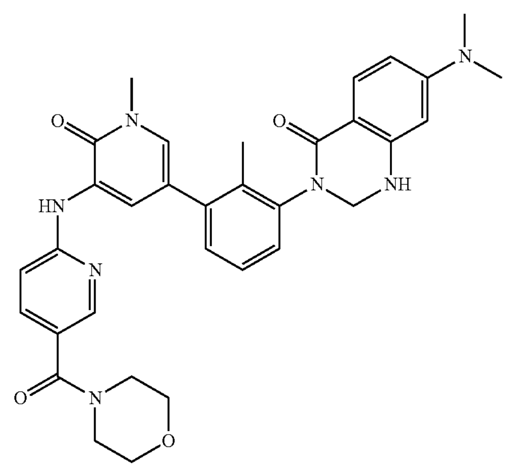 | 7-Dimethylamino-3-(2-methyl-3-{1-methyl-5-[5-(morpholine-4-carbonyl)-pyridin-2-ylamino]-6-oxo-1,6-dihydro-pyridin-3-yl}-phenyl)-2,3-dihydro-1H-quinazolin-4-one | 247.1-250.9 |
| II-2 | 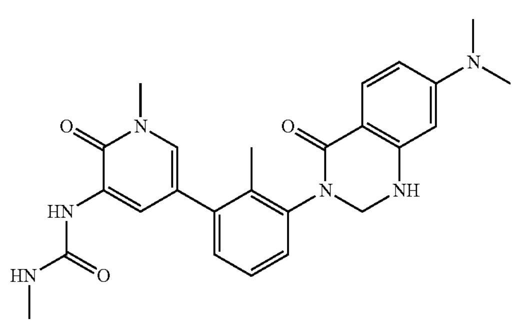 | 1-{5-[3-(7-Dimethylamino-4-oxo-1,4-dihydro-2H-quinazolin-3-yl)-2-methyl-phenyl]-1-methyl-2-oxo-1,2-dihydro-pyridin-3-yl}-3-methyl-urea | 218.5-223.8 |

TABLE I-continued

| Compound # | Structure | Nomenclature | MP |
|---|---|---|---|
| II-3 | 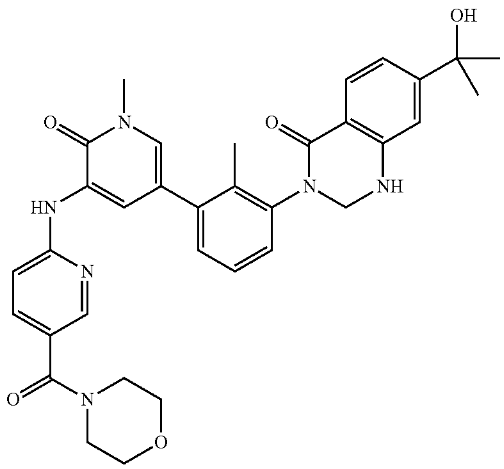 | 7-(1-Hydroxy-1-methyl-ethyl)-3-(2-methyl-3-{1-methyl-5-[5-(morpholine-4-carbonyl)-pyridin-2-ylamino]-6-oxo-1,6-dihydro-pyridin-3-yl}-phenyl)-2,3-dihydro-1H-quinazolin-4-one | 196.0-197.0 |
| II-4 | 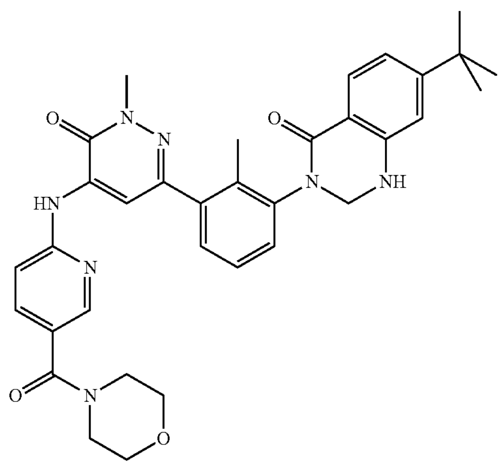 | 7-tert-Butyl-3-(2-methyl-3-{1-methyl-5-[5-(morpholine-4-carbonyl)-pyridin-2-ylamino]-6-oxo-1,6-dihydro-pyridazin-3-yl}-phenyl)-2,3-dihydro-1H-quinazolin-4-one | |
| III-1 | 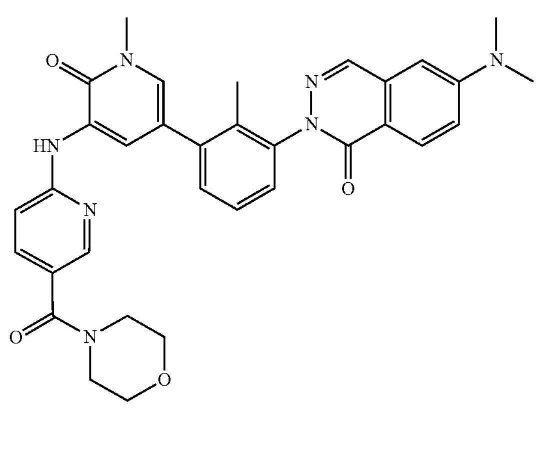 | 6-Dimethylamino-2-(2-methyl-3-{1-methyl-5-[5-(morpholine-4-carbonyl)-pyridin-2-ylamino]-6-oxo-1,6-dihydro-pyridin-3-yl}-phenyl)-2H-phthalazin-1-one | |

TABLE I-continued

| Compound # | Structure | Nomenclature | MP |
|---|---|---|---|
| III-2 | 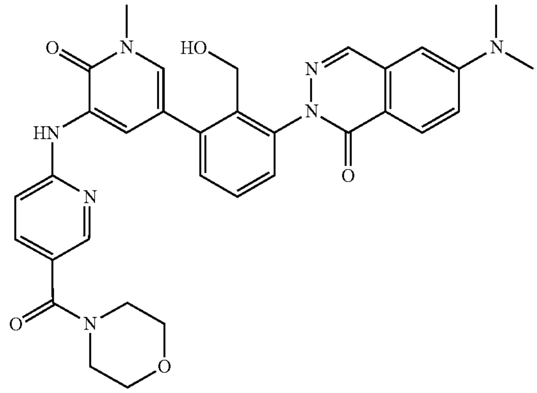 | 6-Dimethylamino-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-phthalazin-1-one | |
| III-3 | 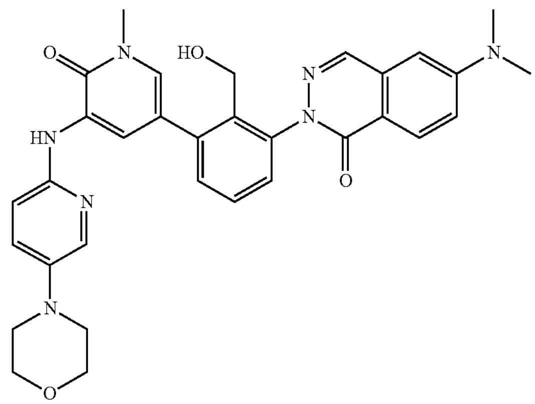 | 6-Dimethylamino-2-{2-hydroxymethyl-3-[1-methyl-5-(5-morpholin-4-yl-pyridin-2-ylamino)-6-oxo-1,6-dihydro-pyridin-3-yl]-phenyl}-2H-phthalazin-1-one | |
| III-4 | 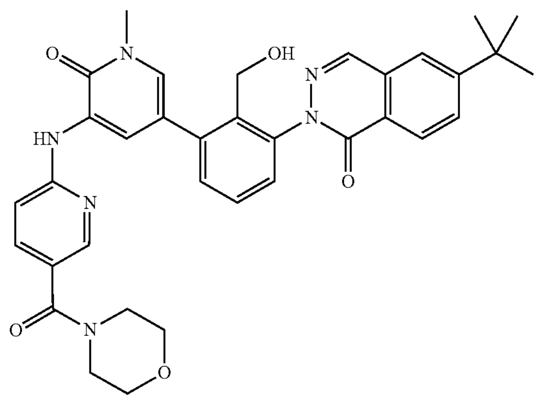 | 6-tert-Butyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-phthalazin-1-one | |
| III-5 | 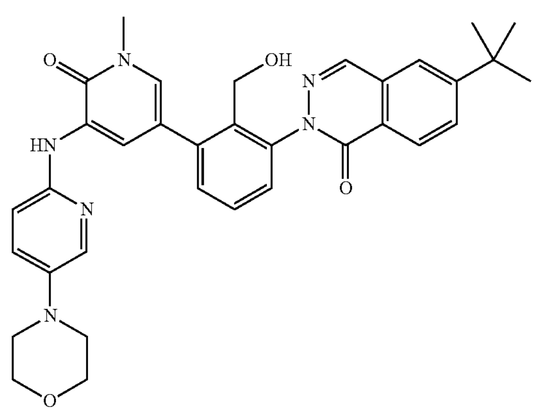 | 6-tert-Butyl-2-{2-hydroxymethyl-3-[1-methyl-5-(5-morpholin-4-yl-pyridin-2-ylamino)-6-oxo-1,6-dihydro-pyridin-3-yl]-phenyl}-2H-phthalazin-1-one | |

TABLE I-continued

| Compound # | Structure | Nomenclature | MP |
|---|---|---|---|
| III-6 | 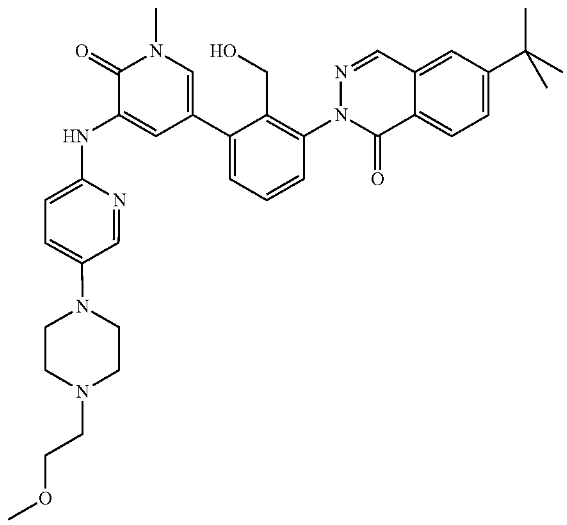 | 6-tert-Butyl-2-[2-hydroxymethyl-3-(5-{5-[4-(2-methoxy-ethyl)-piperazin-1-yl]-pyridin-2-ylamino}-1-methyl-6-oxo-1,6-dihydro-pyridin-3-yl)-phenyl]-2H-phthalazin-1-one | |
| III-7 | 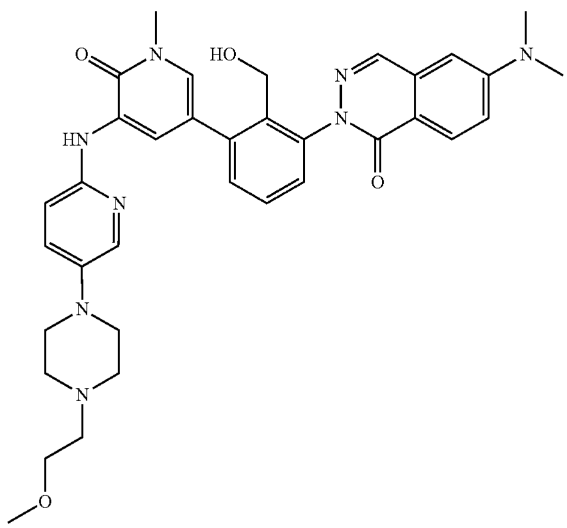 | 6-Dimethylamino-2-[2-hydroxymethyl-3-(5-{5-[4-(2-methoxy-ethyl)-piperazin-1-yl]-pyridin-2-ylamino}-1-methyl-6-oxo-1,6-dihydro-pyridin-3-yl)-phenyl]-2H-phthalazin-1-one | |
| III-8 | 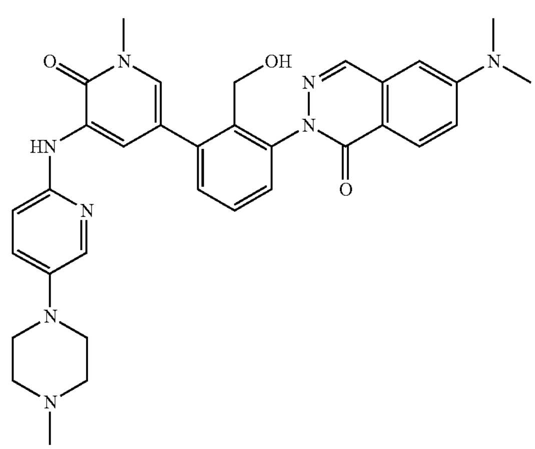 | 6-Dimethylamino-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-phthalazin-1-one | |

TABLE I-continued

| Compound # | Structure | Nomenclature | MP |
|---|---|---|---|
| III-9 | 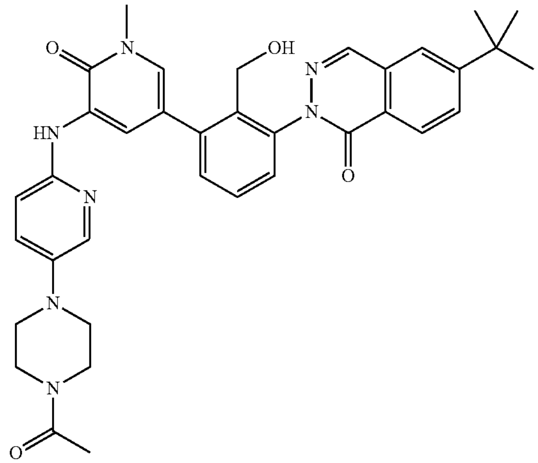 | 2-(3-{5-[5-(4-Acetyl-piperazin-1-yl)-pyridin-2-ylamino]-1-methyl-6-oxo-1,6-dihydro-pyridin-3-yl}-2-hydroxymethyl-phenyl)-6-tert-butyl-2H-phthalazin-1-one | |
| III-10 | 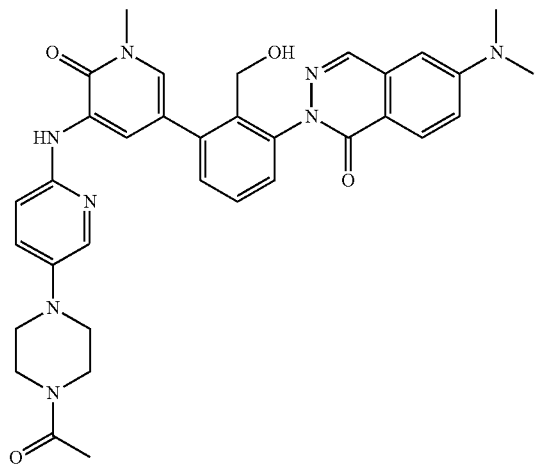 | 2-(3-{5-[5-(4-Acetyl-piperazin-1-yl)-pyridin-2-ylamino]-1-methyl-6-oxo-1,6-dihydro-pyridin-3-yl}-2-hydroxymethyl-phenyl)-6-dimethylamino-2H-phthalazin-1-one | |
| III-11 | 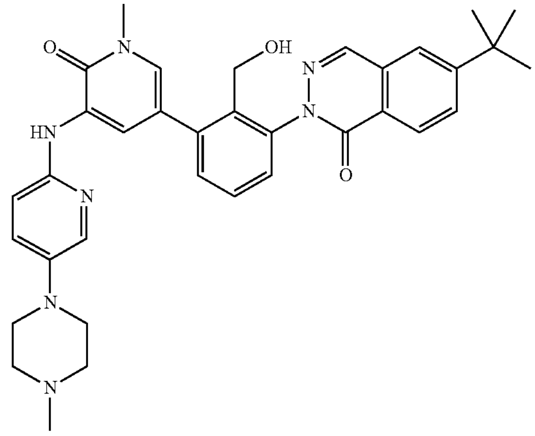 | 6-tert-Butyl-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-phthalazin-1-one | |

TABLE I-continued

| Compound # | Structure | Nomenclature | MP |
|---|---|---|---|
| III-12 | 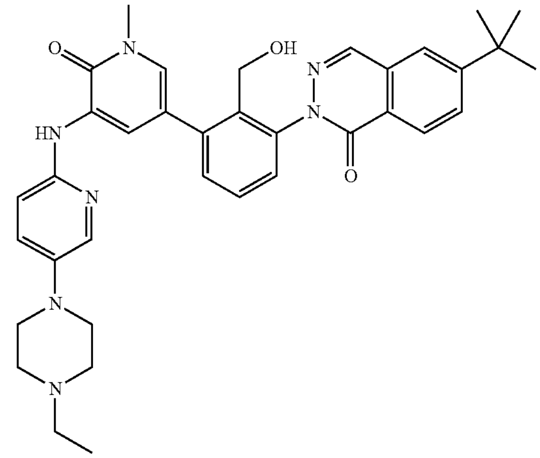 | 6-tert-Butyl-2-(3-{5-[5-(4-ethyl-piperazin-1-yl)-pyridin-2-ylamino)-1-methyl-6-oxo-1,6-dihydro-pyridin-3-yl}-2-hydroxymethyl-phenyl)-2H-phthalazin-1-one | |
| III-13 | 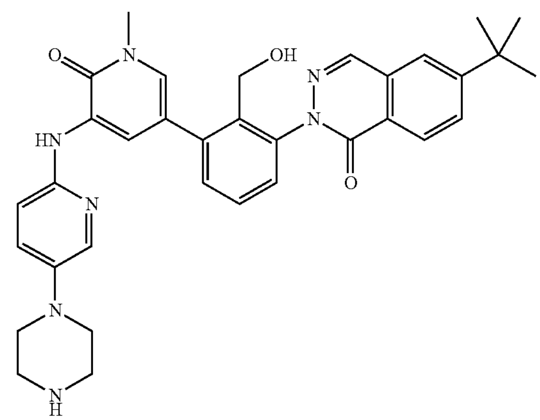 | 6-tert-Butyl-2-{2-hydroxymethyl-3-[1-methyl-6-oxo-5-(5-piperazin-1-yl-pyridin-2-ylamino)-1,6-dihydro-pyridin-3-yl]-phenyl}-2H-phthalazin-1-one | |
| III-14 | 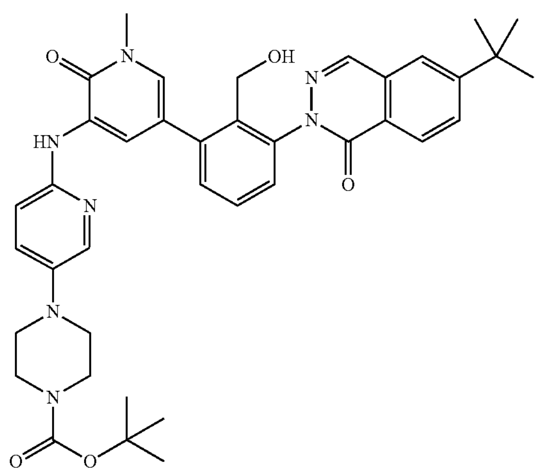 | 4-(6-{5-[3-(6-tert-Butyl-1-oxo-1H-phthalazin-2-yl)-2-hydroxymethyl-phenyl]-1-methyl-2-oxo-1,2-dihydro-pyridin-3-ylamino}-pyridin-3-yl)-piperazine-1-carboxylic acid tert-butyl ester | |

TABLE I-continued

| Compound # | Structure | Nomenclature | MP |
|---|---|---|---|
| IV-1 | 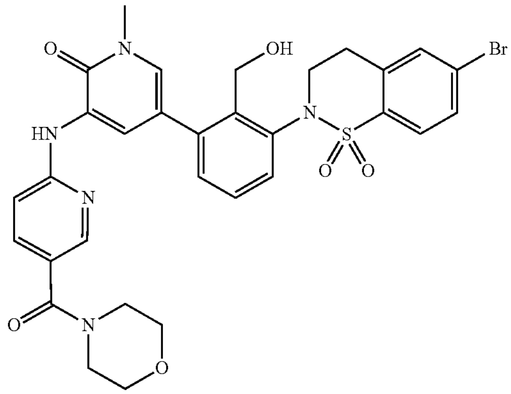 | 5-[3-(6-Bromo-1,1-dioxo-3,4-dihydro-1H-1λ6-benzo[e][1,2]thiazin-2-yl)-2-hydroxymethyl-phenyl]-1-methyl-3-[5-(morpholine-4-carbonyl)-pyridin-2-ylamino]-1H-pyridin-2-one | |
| IV-2 | 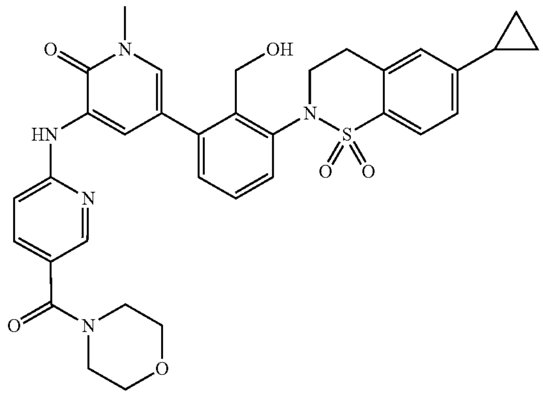 | 5-[3-(6-Cyclopropyl-1,1-dioxo-3,4-dihydro-1H-1λ6-benzo[e][1,2]thiazin-2-yl)-2-hydroxymethyl-phenyl]-1-methyl-3-[5-(morpholine-4-carbonyl)-pyridin-2-ylamino]-1H-pyridin-2-one | |
| IV-3 | 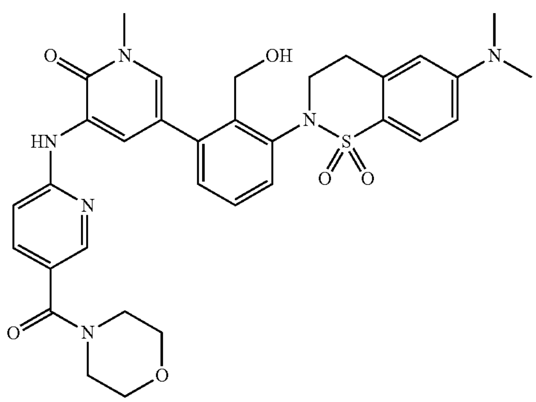 | 5-[3-(6-Dimethylamino-1,1-dioxo-3,4-dihydro 1H-1λ6-benzo[e][1,2]thiazin-2-yl)-2-hydroxymethyl-phenyl]-1-methyl-3-[5-(morpholine-4-carbonyl)-pyridin-2-ylamino]-1H-pyridin-2-one | |
| IV-4 | 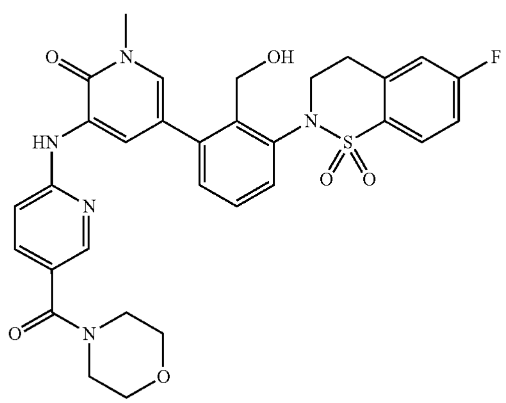 | 5-[3-(6-Fluoro-1,1-dioxo-3,4-dihydro-1H-1λ6-benzo[e][1,2]thiazin-2-yl)-2-hydroxymethyl-phenyl]-1-methyl-3-[5-(morpholine-4-carbonyl)-pyridin-2-ylamino]-1H-pyridin-2-one | |

Pharmacological Activity

The pyrimidine and pyridine derivatives described herein are kinase inhibitors, in particular Btk inhibitors. These inhibitors can be useful for treating one or more diseases responsive to kinase inhibition, including diseases responsive to Btk inhibition and/or inhibition of B-cell proliferation, in mammals. Without wishing to be bound to any particular theory, it is believed that the interaction of the compounds of the invention with Btk results in the inhibition of Btk activity and thus in the pharmaceutical utility of these compounds. Accordingly, the invention includes a method of treating a mammal, for instance a human, having a disease responsive to inhibition of Btk activity, and/or inhibiting B-cell proliferation, comprising administrating to the mammal having such a disease, an effective amount of at least one chemical entity provided herein. An effective concentration may be ascertained experimentally, for example by assaying blood concentration of the compound, or theoretically, by calculating bioavailability. Other kinases that may be affected in addition to Btk include, but are not limited to, other tyrosine kinases and serine/threonine kinases.

Kinases play notable roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

An embodiment includes a method of treating a patient having an autoimmune and/or inflammatory disease, or an acute inflammatory reaction responsive to inhibition of Btk activity and/or B-cell proliferation.

Autoimmune and/or inflammatory diseases that can be affected using compounds and compositions according to the invention include, but are not limited to: psoriasis, allergy, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, and myasthenia gravis, Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., *J. Biol. Chem.* 1998, 274, 1646-1656).

It has also been discovered that BTK inhibitors are useful as chemosensitizing agents, and, thus, are useful in combination with other chemotherapeutic drugs, in particular, drugs that induce apoptosis. Examples of other chemotherapeutic drugs that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Btk activity has also be associated with some leukemias expressing the bcr-abl fusion gene resulting from translocation of parts of chromosome 9 and 22. This abnormality is commonly observed in chronic myelogenous leukemia. Btk is constitutively phosphorylated by the bcr-abl kinase which initiates downstream survival signals which circumvents apoptosis in bcr-abl cells. (N. Feldhahn et al. *J. Exp. Med.* 2005 201(11):1837-1852)

Dosage and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth, pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

EXAMPLES

Example 1

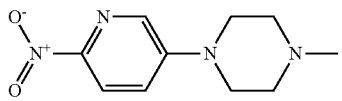

1-Methyl-4-(6-nitro-pyridin-3-yl)-piperazine

To 5-Bromo-2-nitro-pyridine (2.00 g, 9.85 mmol) in 10 mL dimethylsulfoxide was added potassium carbonate (2.72 g, 19.7 mmol), 1-methylpiperazine (1.64 mL, 14.8 mmol), and tetrabutylammonium iodide (36 mg, 0.097 mmol) and was heated at 120° C. for 18 hours. The mixture was made acidic with 1M aq. HCl and was partitioned between dichloromethane and water. The aqueous layer was made basic with 2M aq. sodium carbonate and was extracted with dichloromethane. The organic layer was dried over anhydrous magnesium sulfate, concentrated in vacuo, and was triturated with water to yield 1-Methyl-4-(6-nitro-pyridin-3-yl)-piperazine (1.82 g, 8.19 mmol). MS (ESI) 223.1 (M+H)$^+$.

Example 2

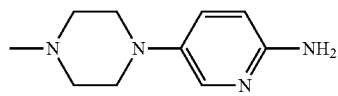

5-(4-Methyl-piperazin-1-yl)-pyridin-2-ylamine

Methyl-4-(6-nitro-pyridin-3-yl)-piperazine (1.748 g, 7.865 mmol) was stirred in 30 mL methanol with 175 mg 10% palladium on carbon under an atmosphere of hydrogen gas for 5 hours. This was filtered and concentrated in vacuo to yield 5-(4-Methyl-piperazin-1-yl)-pyridin-2-ylamine (1.485 g, 7.724 mmol). MS (ESI) 193.1 (M+H)$^+$.

Example 3

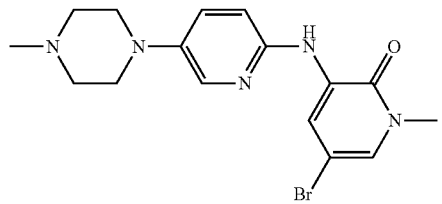

5-Bromo-1-methyl-3-[5-(4-methyl-piperazin-1-yl)-pyridin-2-ylamino]-1H-pyridin-2-one To 5-(4-Methyl-piperazin-1-yl)-pyridin-2-ylamine (1.06 g, 5.53 mmol), 3,5-Dibromo-1-methyl-1H-pyridin-2-one (1.23 g, 4.61 mmol), 4,5-bis(diphenylphosphino)-9,9-dimethylxanthene (400 mg, 0.691 mmol), and cesium carbonate (4.50 g, 13.8 mmol) was added 45 mL 1,4-dioxane and tris (dibenzylidineacetone)dipalladium(0) (422 mg, 0.461 mmol). This was heated in a 120° C. oil bath for 6 hours under argon. This was partitioned between ethylacetate and dilute aqueous sodium bicarbonate. The organic layer was washed with brine, dried over anhydrous magnesium sulfate, concentrated in vacuo, and purified by flash chromatography (gradient elution with 2 to 5% methanol/dichloromethane) to yield 5-Bromo-1-methyl-3-[5-(4-methyl-piperazin-1-yl)-pyridin-2-ylamino]-1H-pyridin-2-one (484 mg, 1.28 mmol). MS (ESI) 380.0 (M+H)$^+$.

Example 4

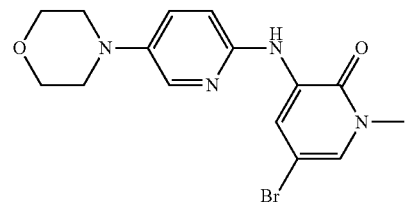

5-Bromo-1-methyl-3-(5-morpholin-4-yl-pyridin-2-ylamino)-1H-pyridin-2-one

This compound was made analogously to 5-Bromo-1-methyl-3-[5-(4-methyl-piperazin-1-yl)-pyridin-2-ylamino]-1H-pyridin-2-one. MS (ESI) 365.0 (M+H)$^+$.

Example 5

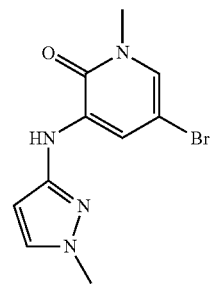

5-Bromo-1-methyl-3-(1-methyl-1H-pyrazol-3-ylamino)-1H-pyridin-2-one 3,5-Dibromo-1-methyl-1H-pyridin-2-one (469 mg, 1.76 mmol), 1-Methyl-1H-pyrazol-3-ylamine (205 mg, 2.11 mmol), tris(dibenzylidineacetone)dipalladium(0) (80 mg, 0.087 mmol), 2,2'-bis(diphenyl phosphino-1,1'-binaphthalene (82 mg, 0.13 mmol), and cesium carbonate (801 mg, 2.46 mmol) were deposited in a sealed vial with 10 mL toluene. This was heated at 130° C. for 18 hours. The resulting mixture was poured into 50 mL water. This was extracted with ethylacetate. The ethylacetate layer was washed with brine, dried over anhydrous magnesium sulfate, filtered, concentrated in vacuo, and purified by flash chromatography (eluted with ethylacete/hexanes) to yield 5-Bromo-1-methyl-3-(1-methyl-1H-pyrazol-3-ylamino)-1H-pyridin-2-one (271 mg, 0.957 mmol). MS (EST) 284.9 (M+H)⁺.

Example 6

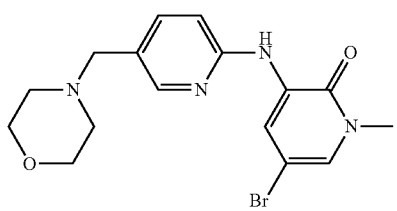

5-Bromo-1-methyl-3-(5-morpholin-4-ylmethyl-pyridin-2-ylamino)-1H-pyridin-2-one

5-Bromo-1-methyl-3-[5-(morpholine-4-carbonyl)-pyridin-2-ylamino]-1H-pyridin-2-one (2.3 g, 5.9 mmol) was dissolved in 30 mL tetrahydrofuran. Borane tetrahydrofuran complex (2.5 g, 29 mmol) was added. After stirring for 18 hours, this was concentrated in vacuo. Ethanol was added. This was refluxed for one hour. This was concentrated in vacuo and purified by flash chromatography to yield 5-Bromo-1-methyl-3-(5-morpholin-4-ylmethyl-pyridin-2-ylamino)-1H-pyridin-2-one (500 mg, 1.32 mmol). MS (ESI) 381.0 (M+H)⁺.

Example 7

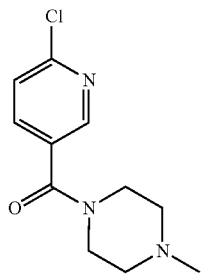

(6-Chloro-pyridin-3-yl)-(4-methyl-piperazin-1-yl)-methanone

To a solution of 6-Chloro-nicotinic acid (3.00 g, 19.0 mmol) in 30 mL dimethylformamide was added (benzotriazol-1-yloxy)tripyrrolidinophosphonium hexafluorophosphate (10.9 g, 20.9 mmol), 1-methylpiperazine (2.30 g, 22.1 mmol). and triethylamine (2.18 g, 21.5 mmol). After stirring for 18 hours, this was partitioned between ethyl acetate and water. The ethylacetate layer was dried over anhydrous sodium sulfate, concentrated in vacuo, and purified by flash chromatography (elution with 3% methanol/dichloromethane) to yield (6-Chloro-pyridin-3-yl)-(4-methyl-piperazin-1-yl)-methanone (2.50 g, 9.33 mmol).

Example 8

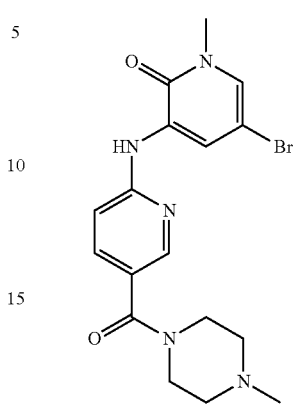

5-Bromo-1-methyl-3-[5-(4-methyl-piperazine-1-carbonyl)-pyridin-2-ylamino]-1H-pyridin-2-one To a solution of (6-Chloro-pyridin-3-yl)-(4-methyl-piperazin-1-yl)-methanone (2.00 g, 7.46 mmol) in 10 mL dimethylformamide was added 3-Amino-5-bromo-1-methyl-1H-pyridin-2-one (1.80 g, 8.95 mmol) and sodium hydride (537 mg, 22.4 mmol). After stirring for 18 hours, this was quenched with water. This was extracted with ethylacetate. The ethylacetate layer was dried over anhydrous sodium sulfate, concentrated in vacuo, and purified by flash chromatography (gradient elution 0 to 5% methanol/dichloromethane) to yield 5-Bromo-1-methyl-3-[5-(4-methyl-piperazine-1-carbonyl)-pyridin-2-ylamino]-1H-pyridin-2-one (900 mg, 1.94 mmol). MS (ESI) 406.0 (M+H)⁺.

Example 9

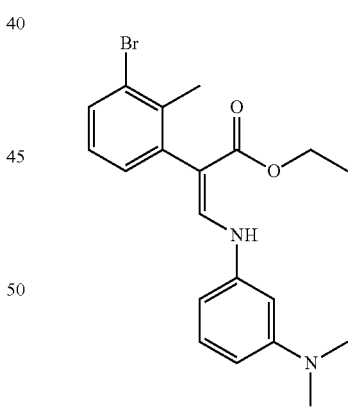

2-(3-Bromo-2-methyl-phenyl)-3-(3-dimethylaminophenylamino)-acrylic acid ethyl ester (3-Bromo-2-methyl-phenyl)-acetic acid benzyl ester (421 mg, 1.32 mmol) was dissolved in ethyl formate (2.5 mL, 31 mmol). Sodium hydride (95%, 67 mg, 2.6 mmol) was added. After stirring for 30 minutes, this was quenched with 1M aq. HCl. This was partitioned between ethyl acetate and water. The ethyl acetate layer was washed with water, washed with brine, dried over anhydrous magnesium sulfate, and concentrated in vacuo.

A portion of this material and N,N-Dimethyl-benzene-1,3-diamine (96 mg, 0.70 mmol) were stirred in 1 mL ethanol for 18 hours. This was concentrated in vacuo and purified by flash chromatography (gradient elution 5 to 20% ethyl acetate/hexanes) to yield 2-(3-Bromo-2-methyl-phenyl)-3-(3-dimethylamino-phenylamino)-acrylic acid ethyl ester (164 mg, 0.407 mmol). MS (ESI) 405.0 (M+H)+.

Example 10

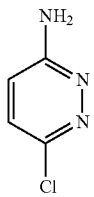

6-Chloro-pyridazin-3-ylamine 3,6-Dichloro-pyridazine (7.5 g, 50.35 mmol) was dissolved in ethanolic ammonia (100 mL) and heated at (130° C.) for overnight in pressure vessel. Then the ethanol was evaporated under reduced pressure and crude purified by silica gel (230-400 mesh) flash chromatography using EtOAc/Hexane (6:4) to afford the title compound (4 g, 61%) as a solid.

Example 11

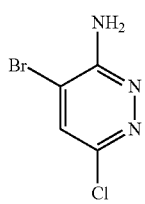

4-Bromo-6-chloro-pyridazin-3-ylamine

To a solution of 6-Chloro-pyridazin-3-ylamine (4 g, 31 mmol) in methanol (60 mL) was added NaHCO$_3$ (5.2 g, 62 mmol). The reaction mixture was stirred for 30 minutes at RT then Br$_2$ (4.9 g, 31 mmol) was added drop wise. Then the resulting reaction mixture was stirred additionally for 16 h at RT. After completion of reaction, the reaction mass concentrated under reduced pressure, crude purified by silica gel (100-200 mesh) chromatography using EtOAc/Hexane (8:2) to afford 4-Bromo-6-chloro-pyridazin-3-ylamine (2.3 g, 36%) as a solid.

Example 12

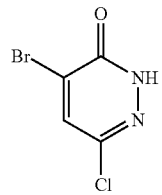

4-Bromo-6-chloro-2H-pyridazin-3-one

To a cooled solution (0-5° C.) of NaNO$_2$ (1 g, 13.20 mmol) in conc. H$_2$SO$_4$ (15 mL) was added 4-Bromo-6-chloro-pyridazin-3-ylamine (2.3 g, 11 mmol) in 50 mL of acetic acid. Then the reaction mixture was stirred for 1 h at 20° C. followed by addition of water (75 mL) and stirring continued for 5 h at RT. The reaction mixture extracted with EtOAc, dried over Na$_2$SO$_4$, concentrated under reduced pressure and crude purified by silica gel (100-200 mesh) chromatography using EtOAc/Hexane (8:2) to afford 4 (2.2 g, 95%) yellowish solid.

Example 13

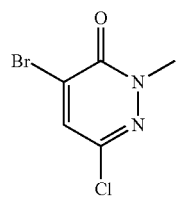

4-Bromo-6-chloro-2-methyl-2H-pyridazine-3-one

4-Bromo-6-chloro-2H-pyridazin-3-one (5.02 g, 23.97 mmol) was dissolved in 40 ml dimethylformamide. Cesium carbonate (9.37 g, 28.76 mmol) was added. After 5 min, iodomethane (5.103 g, 35.95 mmol) was added dropwise over 20 min. The reaction mixture was stirred 3 hours at room temperature. The precipitate was filtered off and concentrated and the resulting residue was treated with 20 ml dichloromethane. The insoluble material was filtered off again and washed with dichloromethane. The filtrate was concentrated in vacuo to yield 4-Bromo-6-chloro-2-methyl-2H-pyridazine-3-one (5.223 g, 23.37 mmol). MS (ESI) 224.9 (M+H)+

Example 14

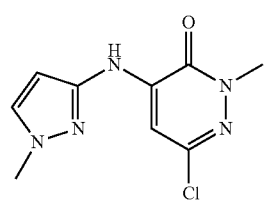

6-Chloro-2-methyl-4-(1-methyl-1H-pyrazol-3-ylamino)-2H-pyridazin-3-one

Methyl-1H-pyrazol-3-amine (806 mg, 8.3 mmol) was dissolved in 40 ml dioxane. Potassium tert-butoxide (1.793 g, 15.98 mmol) was added. Finally 4-Bromo-6-chloro-2-methyl-2H-pyridazine-3-one (1.7 g, 7.61 mmol) was added and the mixture was stirred for 3 hours at ambient temperature. The reaction mixture was transferred into an 150 ml Erlenmeyer flask and acidified with 15 ml 1 M aqueous hydrochloric solution, then treated with a saturated sodium bicarbonate solution until the pH reached about 8. It was extracted twice with each 100 ml of dichloromethane; and the organic phase was dried with sodium sulfate, filtered, and concentrated in vacuo to give 1.5 g of a light orange solid. This crude material was triturated with a mixture of dichloromethane and hexane. The suspension was filtered off and the resulting filter cake was dried under high vacuum to yield 6-Chloro-2-methyl-4-(1-methyl-1H-pyrazol-3-ylamino)-2H-pyridazin-3-one (967 mg, 4.03 mmol). MS (ESI) 240.0 (M+H)$^+$

Example 15

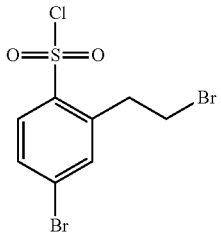

4-Bromo-2-(2-bromo-ethyl)-benzenesulfonyl chloride

Chlorosulfonic acid (17 mL) was added dropwise to 1-bromo-3-(2-bromo-ethyl)-benzene (5 g, 19 mmol) at 0° C. The mixture was stirred at 0° C. for 1 h then an additional 3 h at The mixture was poured into an ice-water slowly and extracted with methylene chloride, and the combined organic layers were evaporated under reduced pressure to give 4.3 g of crude 4-Bromo-2-(2-bromo-ethyl)-benzenesulfonyl chloride which was used directly for next reaction. MS (ESI) 342.9 (M-Cl+OH)$^-$.

Example 16

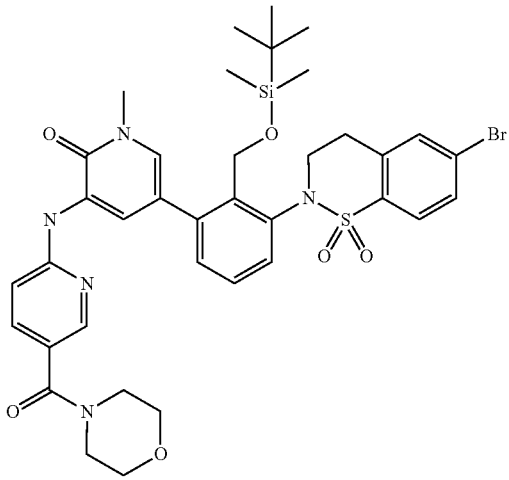

5-[3-(6-Bromo-1,1-dioxo-3,4-dihydro-1H-1lambda*6*-benzo[e][1,2]thiazin-2-yl)-2-(tert-butyl-dimethyl-silanyloxymethyl)-phenyl]-3-[5-(morpholine-4-carbonyl)-pyridin-2-ylamino]-1H-pyridin-2-one The mixture of 5-[3-Amino-2-(tert-butyl-dimethyl-silanyloxymethyl)-phenyl]-1-methyl-3-[5-(morpholine-4-carbonyl)-pyridin-2-ylamino]-1H-pyridin-2-one (0.2 g, 0.36 mmol), 4-bromo-2-(2-bromo-ethyl)-benzenesulfonyl chloride (0.4 g, 1.08 mmol) and DIPEA (1 mL) in dichloroethane (10 mL) was microwaved at 120° C. for 30 min, then added 4-bromo-2-(2-bromo-ethyl)-benzenesulfonyl chloride (0.4 g, 1.08 mmol) and DIPEA (1 mL) and microwaved at 120° C. for 30 min. After repeating this process three times, the mixture was concentrated to afford a dark residue. Purification by silica gel chromatography (methylene chloride/acetone) afforded 0.15 g of 5-[3-(6-Bromo-1,1-dioxo-3,4-dihydro-1H-1lambda*6*-benzo[e][1,2]thiazin-2-yl)-2-(tert-butyl-dimethyl-silanyloxymethyl)-phenyl]-3-[5-(morpholine-4-carbonyl)-pyridin-2-ylamino]-1H-pyridin-2-one as a pale solid MS (ESI) 796.2 (M+H)$^+$.

Example 17

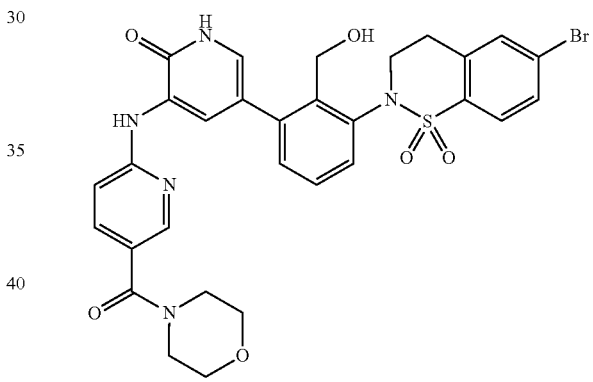

5-[3-(6-Bromo-1,1-dioxo-3,4-dihydro-1H-1lambda*6*-benzo[e][1,2]thiazin-2-yl)-2-hydroxymethyl-phenyl]-1-methyl-3-[5-(morpholine-4-carbonyl)-pyridin-2-ylamino]-1H-pyridin-2-one The mixture of 5-[3-(6-Bromo-1,1-dioxo-3,4-dihydro-1H-1lambda*6*-benzo[e][1,2]thiazin-2-yl)-2-(tert-butyl-dimethyl-silanyloxymethyl)-phenyl]-3-[5-(morpholine-4-carbonyl)-pyridin-2-ylamino]-1H-pyridin-2-one (0.05 g, 0.06 mmol), conc. HCl (1 mL) in methanol (10 mL) was stirred rt for 30 min. The mixture was neutralized with solid Na$_2$CO$_3$ and concentrated to afford a dark residue. Purification by silica gel chromatography (methylene chloride/acetone) afforded 0.01 g of 5-[3-(6-bomo-1,1-dioxo-3,4-dihydro-1H-1lambda*6*-benzo[e][1,2]thiazin-2-yl)-2-(tert-butyl-dimethyl-silanyloxymethyl)-phenyl]-1-methyl-3-[5-(morpholine-4-carbonyl)-pyridin-2-ylamino]-1H-pyridin-2-one as a pale solid MS (ESI) 682.0 (M+H)+.

Example 18

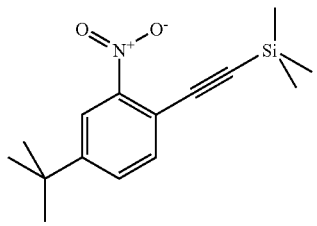

(4-tert-Butyl-2-nitro-phenylethynyl)-trimethyl-silane

To Trifluoro-methanesulfonic acid 4-tert-butyl-2-nitrophenyl ester (3.715 g, 11.35 mmol), dichlorobis(triphenylphosphine)palladium(II) (336 mg, 0.478 mmol), cuprous iodide (168 mg, 0.882 mmol) was added dimethylformamide (45 mL), triethylamine (1.72 g, 17.0 mmol), and trimethylsilylacetylene (2.229 g, 22.70 mmol). The resulting mixture was heated at 90° C. under an atmosphere of nitrogen for 15 minutes. This was partitioned between ethylacetate and water. The ethylacetate layer was washed with brine, dried over anhydrous $MgSO_4$, concentrated in vacuo, and purified by flash chromatography with elution with $CH_2Cl_2$ to yield (4-tert-Butyl-2-nitro-phenylethynyl)-trimethyl-silane (3.193 g, 11.61 mmol).

Example 19

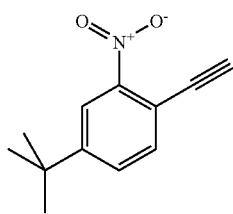

4-tert-Butyl-1-ethynyl-2-nitro-benzene (4-tert-Butyl-2-nitro-phenylethynyl)-trimethyl-silane (3.167 g, 11.51 mmol) and potassium carbonate (3.18 g, 23.0 mmol) were stirred in 75 mL methanol for 20 minutes. The resulting mixture was partitioned between ethylacetate and water. The ethylacetate layer was washed with brine, dried over anhydrous $MgSO_4$, concentrated in vacuo, and purified by flash chromatography with gradient elution with 0 to 5% ethylacetate/hexanes to yield 4-tert-Butyl-1-ethynyl-2-nitrobenzene (1.910 g, 9.398 mmol).

Example 20

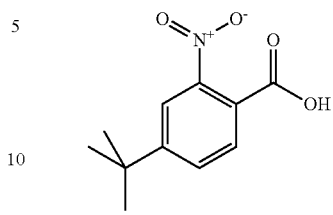

4-tert-Butyl-2-nitro-benzoic acid 4-tert-Butyl-1-ethynyl-2-nitro-benzene (1.662 g, 8.176 mmol) was dissolved in 20 mL carbon tetrachloride, 20 mL acetonitrile, and 40 mL water. Periodic acid (9.322 g, 40.89 mmol) was added followed by ruthenium(III)chloride hydrate (85 mg, 0.41 mmol). After stirring of 90 minutes, the resulting mixture was diluted with water and extracted with three portions of dichloromethane. The combined dichloromethane layers wee dried over anhydrous $MgSO_4$, and concentrated in vacuo to yield 4-tert-Butyl-2-nitro-benzoic acid (1.924 g, 86.19 mmol).

Example 21

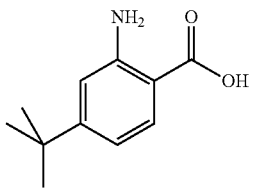

2-Amino-4-tert-butyl-benzoic acid 4-tert-Butyl-2-nitro-benzoic acid (199 mg, 8.91 mmol), and 10% palladium on carbon (40 mg) were stirred in 6 mL ethanol under an atmosphere of hydrogen for 3 hours. The resulting mixture was filtered and concentrated in vacuo to yield 2-Amino-4-tert-butyl-benzoic acid (177 mg, 0.916 mmol).

Example 22

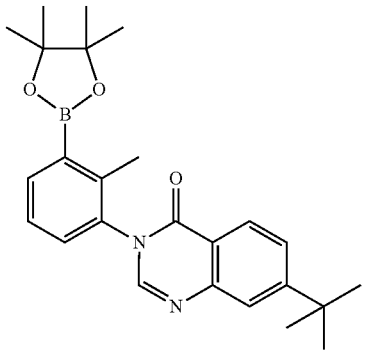

7-tert-Butyl-3-[2-methyl-3-(4,4,5,5-tetramethyl-[1,3,2]dioxaborolan-2-yl)-phenyl]-3H-quinazolin-4-one A solution of 2-Amino-4-tert-butyl-benzoic acid (78 mg, 0.41 mmol) in 2 mL trimethylorthoformate was heated to 105° C. for 30 minutes. The resulting solution was concentrated in vacuo. 2-Methyl-3-(4,4,5,5-tetramethyl-[1,3,2]dioxaborolan-2-yl)-phenylamine (100 mg, 0.41 mmol) in 2 mL toluene was added. The resulting mixture was heated at reflux for 1 hour, concentrated in vacuo, and purified by flash chromatography (15% ethylacetate/hexanes) to yield 7-tert-Butyl-3-[2-methyl-3-(4,4,5,5-tetramethyl-[1,3,2]dioxaborolan-2-yl)-phenyl]-3H-quinazolin-4-one (68 mg, 0.16 mmol). MS (ESI) 419.2 (M+H)+.

Example 23

7-tert-Butyl-3-(2-methyl-3-{1-methyl-5-[5-(morpholine-4-carbonyl)-pyridin-2-ylamino]-6-oxo-1,6-dihydro-pyridazin-3-yl}-phenyl)-3H-quinazolin-4-one A solution of 6-Chloro-2-methyl-4-[5-(morpholine-4-carbonyl)-pyridin-2-ylamino]2H-pyridazin-3-one (56 mg, 0.16 mmol), 7-tert-Butyl-3-[2-methyl-3-(4,4,5,5-tetramethyl-[1,3,2]dioxaborolan-2-yl)-phenyl]-3H-quinazolin-4-one (68 mg, 0.16 mmol), tetrakis(triphenylphosphine)palladium(0) (19 mg, 0.016 mmol), and sodium carbonate (52 mg, 0.49 mmol) in 2 mL 1,2-dimethoxyethane and 1 mL water was heated on the microwave synthesizer at 170° C. for 12.5 minutes. The resulting mixture was partitioned between ethylacetate and water. The ethylacetate layer was washed with brine, dried over anhydrous MgSO4, concentrated in vacuo, and purified by preparative TLC (10% MeOH/CH2Cl2) to yield 7-tert-Butyl-3-(2-methyl-3-{1-methyl-5-[5-(morpholine-4-carbonyl)-pyridin-2-ylamino]-6-oxo-1,6-dihydro-pyridazin-3-yl}-phenyl)-3H-quinazolin-4-one (26.4 mg, 0.044 mmol). MS (ESI) 606 (M+H)+.

Example 24

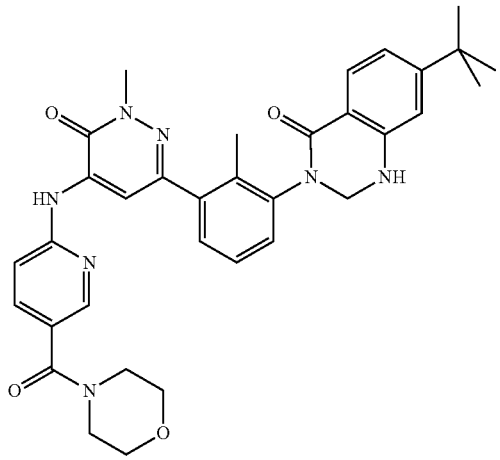

7-tert-Butyl-3-(2-methyl-3-{1-methyl-5-[5-(morpholine-4-carbonyl)-pyridin-2-ylamino]-6-oxo-1,6-dihydro-pyridazin-3-yl}-phenyl)-2,3-dihydro-1H-quinazolin-4-one To a mixture of 7-tert-Butyl-3-(2-methyl-3-{1-methyl-5-[5-(morpholine-4-carbonyl)-pyridin-2-ylamino]-6-oxo-1,6-dihydro-pyridazin-3-yl}-phenyl)-3H-quinazolin-4-one (11 mg, 0.018 mmol) and sodium cyanoborohydride (1.3 mg, 0.019 mmol) in 1 mL methanol was added 1 drop of 2M hydrochloric acid in methanol to bring the pH to 3. After stirring for 45 minutes, the resulting mixture was partitioned between ethylacetate and dilute aqueous NaHCO3. The ethylacetate layer was washed with brine, dried over anhydrous MgSO4, concentrated in vacuo, and purified by preparative TLC (5% MeOH/CH2Cl2) to yield 7-tert-Butyl-3-(2-methyl-3-{1-methyl-5-[5-(morpholine-4-carbonyl)-pyridin-2-ylamino]-6-oxo-1,6-dihydro-pyridazin-3-yl}-phenyl)-2,3-dihydro-1H-quinazolin-4-one (6.5 mg, 0.011 mmol). MS (EST) 608 (M+H)+.

Example 25

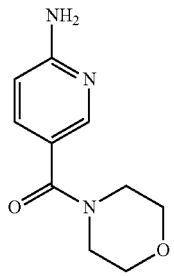

(6-Amino-pyridin-3-yl)-morpholin-4-yl-methanone

To a solution of morpholine (9.00 g, 103 mmol) in 400 mL ethanol was added N-(3-Dimethylaminopropyl)-N'-ethylcarbodiimide hydrochloride (10.0 g, 52.2 mmol), 1-hydroxybenzotriazole (7.00 g, 51.8 mmol), and 6-aminonicotinic acid (6.00 g, 43.4 mmol). After stirring for 18 hours, the resulting solid was filtered. This was triturated with a mixture of 100 mL methanol and 100 mL dichloromethane to yield (6-Amino-pyridin-3-yl)-morpholin-4-yl-methanone (3.08 g, 14.9 mmol). MS (ESI) 208.1 (M+H)+.

Example 26

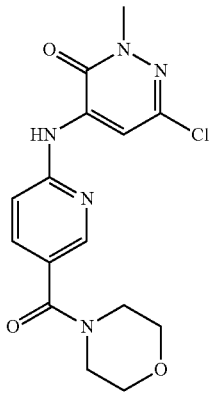

6-Chloro-2-methyl-4-[5-(morpholine-4-carbonyl)-pyridin-2-ylamino]-2H-pyridazin-3-one (6-Amino-pyridin-3-yl)-morpholin-4-yl-methanone (2.921 g, 14.11 mmol) was suspended in 50 mL dimethylformamide and cooled to 0° C. Sodium hydride 60% suspension in mineral oil (847 mg, 21.2 mmol) was added. This was stirred at room temperature for 30 minutes and was cooled to 0° C. 4,6-Dichloro-2-methyl-2H-pyridazin-3-one (1.256 g, 7.056 mmol) was added. After 2 hours, this was partitioned between saturated aqueous ammonium chloride solution and ethylacetate. The ethylacetate layer was dried over anhydrous MgSO4, concentrated in vacuo, and purified by flash chromatography (2% MeOH/CH2Cl2) to yield 6-Chloro-2-methyl-4-[5-(morpholine-4-carbonyl)-pyridin-2-ylamino]-2H-pyridazin-3-one (732 mg, 2.09 mmol). MS (ESI) 350.1 (M+H)+.

Example 27

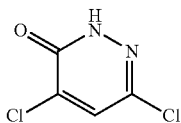

4,6-Dichloro-2H-pyridazin-3-one 3,4,6-Trichloro-pyridazine (34.39 g, 187.5 mmol) in 100 mL acetic acid was heated at reflux for three hours. The resulting mixture was cooled to room temperature and filtered. The filtrate was diluted with ethylacetate. This was washed three times with water, washed with brine, dried over anhydrous MgSO4, concentrated in vacuo, and purified by flash chromatography (30% ethylacetate/hexanes) to yield 4,6-Dichloro-2H-pyridazin-3-one (6.143 g, 37.23 mmol). MS (ESI) 165.0 (M+H)+.

Example 28

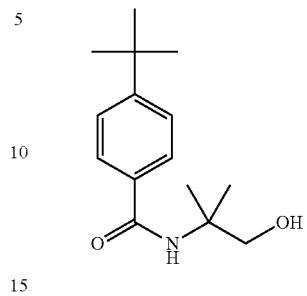

4-tert-Butyl-N-(2-hydroxy-1,1-dimethyl-ethyl)-benzamide 30.95 g (347 mmol) of 2-amino-2-methyl-1-propanol was weighed into a 500 mL Erlenmeyer flask fitted with a stir bar and septum. Added 200 mL CH2Cl2. Established and maintained nitrogen atmosphere. Stirred the solution in an ice/water bath. Added 34 mL (174 mmol) of 4-tert-butylbenzoyl chloride dropwise over 30 min. A white precipitate formed. Stirred at room temperature overnight. Removed the solids by filtration and washed with CH2Cl2. Removed the solvent from the filtrate on rotavap and dried at 60°/4 torr to obtain 45.79 g of the title compound as a light yellow resin. MS (ESI) 248 (M–H)−.

Example 29

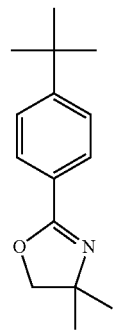

2-(4-tert-Butyl-phenyl)-4,4-dimethyl-4,5-dihydro-oxazole

All of the 4-tert-butyl-N-(2-hydroxy-1,1-dimethyl-ethyl)-benzamide prepared above (174 mmol) was charged into a 500 mL round bottom flask fitted with a stir bar and septum. Established and maintained nitrogen atmosphere. Added 50 mL (685 mmol) of thionyl chloride dropwise over 20 min. Warmed the flask with a heat gun to dissolve some of the resin and initiate the reaction. The reaction mixture solidified. Warmed the flask with a heat gun to dissolve all the solids. Cooled to room temperature. Poured the reaction solution in a thin stream into 500 mL of stirred Et2O. A white precipitate formed. Collected the precipitate by filtration and washed thoroughly with Et2O. Dissolved the collected solids in 300 mL water and neutralized with 25% NaOH. Extracted the yellow aqueous solution with 2×200 mL Et2O. Washed the yellow extracts with 200 brine, dried over MgSO$_4$, and removed the solvent on rotavap to obtain 28.50 g of the title compound as a waxy white solid. MS (ESI) 232 (M+H)$^+$.

Example 30

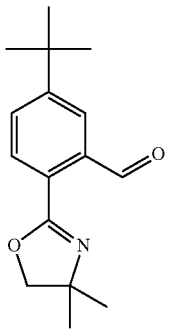

5-tert-Butyl-2-(4,4-dimethyl-4,5-dihydro-oxazol-2-yl)-benzaldehyde

An oven dried 250 mL 3-neck round bottom flask was fitted with a thermometer, stir bar, septum, and nitrogen inlet. Added 8.02 g (34.7 mmol) of 2-(4-tert-butyl-phenyl)-4,4-dimethyl-4,5-dihydro-oxazole. Established and maintained N$_2$ atmosphere. Added 100 mL of anhydrous THF. Cooled the clear solution to −78°. Stirred rapidly and added 17 mL (43 mmol) of a 2.5 M solution of n-butyllithium in hexane dropwise over 10 minutes. Stirred the clear amber solution at −20° for 4 hr. The reaction mixture became red-amber and cloudy. Cooled the mixture to −78°. Stirred rapidly and added 12 mL of DMF dropwise at a rate to keep the temperature below −60°. Stirred at −78° for 15 min. Stirred at −20° for 1 hr. Stirred at room temperature for 1 hr. Quenched with 100 mL of 0.5 M aqueous KHSO$_4$. The aqueous phase was still strongly basic. Added more 1.0 M KHSO$_4$ until the pH was ~2. Diluted the two phase solution with 300 mL Et$_2$O. Separated phases and extracted the aqueous phase with 100 mL Et$_2$O. Washed the combined organic phases with 200 mL brine and dried over K$_2$CO$_3$. Filtered through 120 g of silica gel and washed through with 300 mL Et$_2$O to remove baseline impurities. Removed the solvent on rotavap to obtain 8.18 g of the title compound as a clear yellow liquid. MS (ESI) 260 (M+H)$^+$.

Example 31

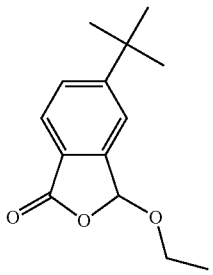

5-tert-Butyl-3-ethoxy-3H-isobenzofuran-1-one 3.66 g (14.1 mmol) of 5-tert-Butyl-2-(4,4-dimethyl-4,5-dihydro-oxazol-2-yl)-benzaldehyde was weighed into a 200 mL round bottom flask fitted with a stir bar and reflux condenser. Added 75 mL of ethanol and stirred to obtain a clear solution. Added 50 mL of 50% aqueous sulfuric acid. Stirred at reflux for 22 hr. Poured the reaction mixture into 400 mL water. Extracted the aqueous mixture with 2×200 mL CH$_2$Cl$_2$. Combined the organic extracts and washed with 200 mL brine. Dried over Na$_2$SO$_4$ and removed the solvent on rotavap. Dried under high vacuum to obtain 2.9 g of the title compound as an off-white solid. MS (ESI) 235 (M+H)$^+$.

Example 32

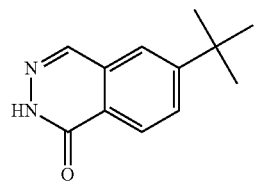

6-tert-Butyl-2H-phthalazin-1-one 2.9 g (12 mmol) of 5-tert-butyl-3-ethoxy-3H-isobenzofuran-1-one was weighed into a 50 mL round bottom flask fitted with a stir bar and cap. Added 10 mL (130 mmol) of hydrazine monohydrate. Added 15 mL of glacial acetic acid. Stirred at 100° overnight. Poured the reaction mixture into 200 mL of stirred water. Collected the solids by filtration and washed with water. Dried under high vacuum to obtain 2.24 g of the title compound as an off-white solid. MS (ESI) 203 (M+H)$^+$.

Example 33

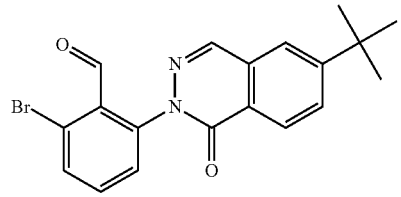

2-Bromo-6-(6-tert-butyl-1-oxo-1H-phthalazin-2-yl)-benzaldehyde 5.90 g (22.4 mmol) of 2,6-dibromobenzaldehyde, 1.80 g (8.90 mmol) of 6-tert-butyl-2H-phthalazin-1-one, 6.02 g (18.5 mmol) of cesium carbonate, 179 mg (0.940 mmol) of copper(I) iodide, and 428 mg (1.87 mmol) of 4,7-dimethoxy-1,10-phenanthroline were weighed into a 100 mL reaction flask fitted with a stir bar and septum cap. Added 50 mL of anhydrous dioxane. Purged the reaction mixture with nitrogen for 15 min. Stirred at 100° for 18 h. Partitioned the reaction mixture between 200 mL of 10% MeOH/CH$_2$Cl$_2$ and 200 mL of water. Separated phases and extracted the aqueous phase with 2×100 mL of 10% MeOH/CH$_2$Cl$_2$. The combined organic extracts were washed with 200 mL of brine, dried over Na$_2$SO$_4$, and the solvent was removed on rotavap. Purified the crude by flash chromatography on silica gel to obtain 2.37 g of the title compound as an off-white solid. MS (ESI) doublet 385, 387 (M+H)$^+$.

Example 34

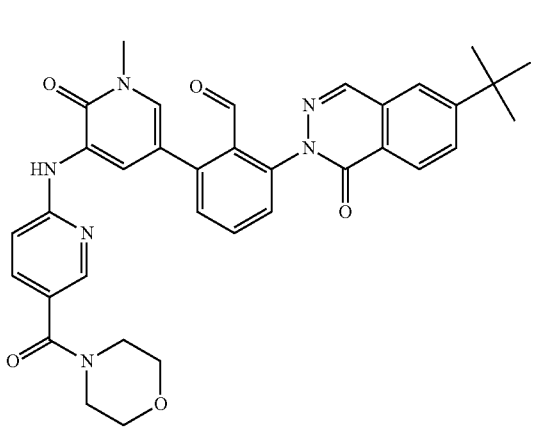

2-(6-tert-Butyl-1-oxo-1H-phthalazin-2-yl)-6-{1-methyl-5-[5-(morpholine-4-carbonyl)-pyridin-2-ylamino]-6-oxo-1,6-dihydro-pyridin-3-yl}-benzaldehyde 149 mg (0.338 mmol) of 1-methyl-3-[5-(morpholine-4-carbonyl)-pyridin-2-ylamino]-5-(4,4,5,5-tetramethyl-1,3,2-dioxaborolan-2-yl)-1H-pyridin-2-one and 116 mg (0.301 mmol) of 2-bromo-6-(6-tert-butyl-1-oxo-1H-phthalazin-2-yl)-benzaldehyde were weighed into a 4 mL reaction vial fitted with a stir bar and septum cap. Added 2.5 mL of dioxane. Added 0.33 mL (0.92 mmol) of an 0.91 g/mL solution of cesium carbonate in water. The mixture was sparged with nitrogen for 10 min. Added 13 mg (0.016 mmol) of [1,1'-bis(diphenylphosphino)ferrocene]palladium(II) chloride 1:1 complex with dichloromethane. The mixture was sparged with nitrogen for 5 min. Sealed the vial with a cap and stirred at 95° for 90 min. Cooled the reaction to room temperature, diluted with 15 mL CH$_2$Cl$_2$ and dried over Na$_2$SO$_4$. Filtered through a 0.45 µM syringe filter and removed the solvent on rotavap. Purified the crude by flash chromatography on silica gel to obtain 129 mg of the title compound as a light yellow solid. MS (ESI) 619 (M+H)$^+$.

Example 35

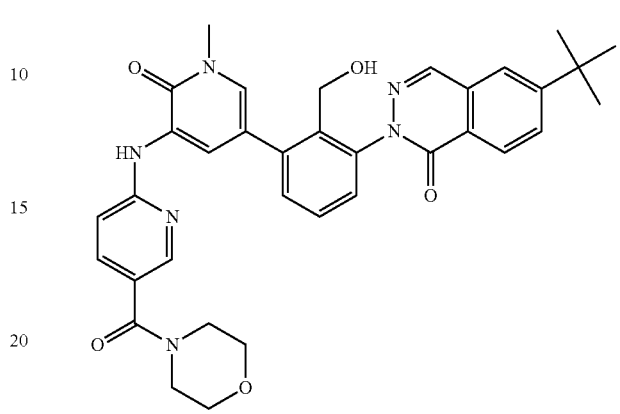

6-tert-Butyl-2-(2-hydroxymethyl-3-{1-methyl-5-[5-(morpholine-4-carbonyl)-pyridin-2-ylamino]-6-oxo-1,6-dihydro-pyridin-3-yl}-phenyl)-2H-phthalazin-1-one 121 mg (0.20 mmol) of 2-(6-tert-butyl-1-oxo-1H-phthalazin-2-yl)-6-{1-methyl-5-[5-(morpholine-4-carbonyl)-pyridin-2-ylamino]-6-oxo-1,6-dihydro-pyridin-3-yl}-benzaldehyde was weighed into a 20 mL reaction vial fitted with a stir bar and septum. Added 4 mL of CH$_2$Cl$_2$ and 2 mL MeOH and stirred to obtain a clear amber solution. Added 1.1 mL (0.29 mmol) of a freshly prepared 10 mg/mL solution of sodium borohydride in MeOH. Stirred at room temperature for 3 hr. Quenched the reaction with 5 mL of saturated aqueous NH$_4$Cl. Added 5 mL of CH$_2$Cl$_2$ to the reaction mixture and separated phases. Washed the organic phase with 5 mL brine, dried over Na$_2$SO$_4$, and removed the solvent on rotavap. Added 2 mL acetonitrile to the residue and immersed the vial in an ultrasonic bath. The residue dissolved momentarily, then a white precipitate rapidly crystallized out of solution. Added 5 mL Et$_2$O to the mixture and collected the precipitate by filtration. Dried under high vacuum to obtain 95 mg of the title compound as an off-white solid. MS (ESI) 621 (M+H)$^+$.

General Scheme 1.

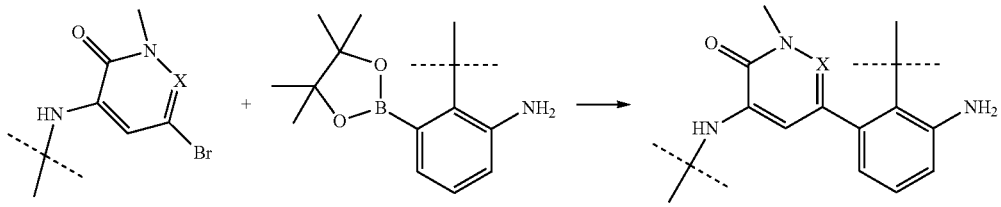

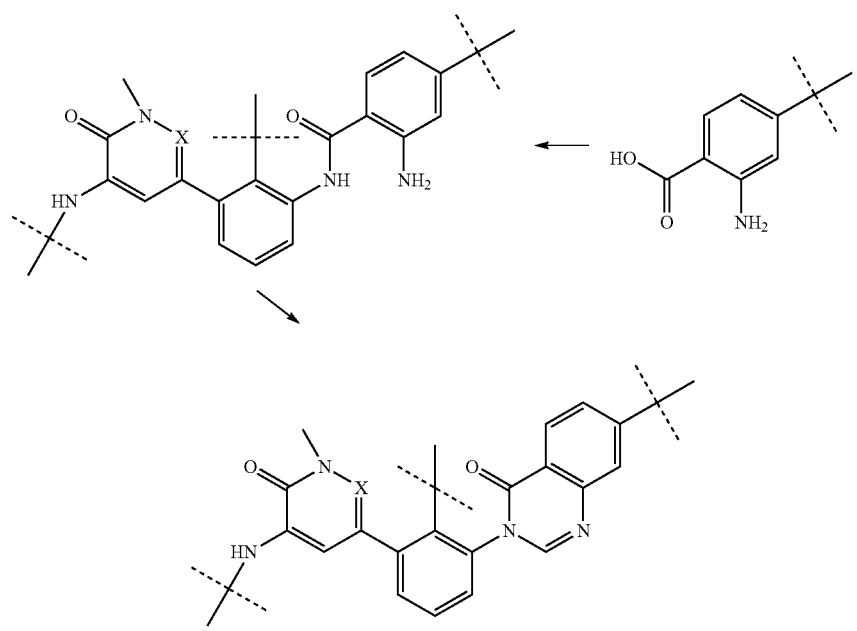
X = CH or N
General Scheme 2.
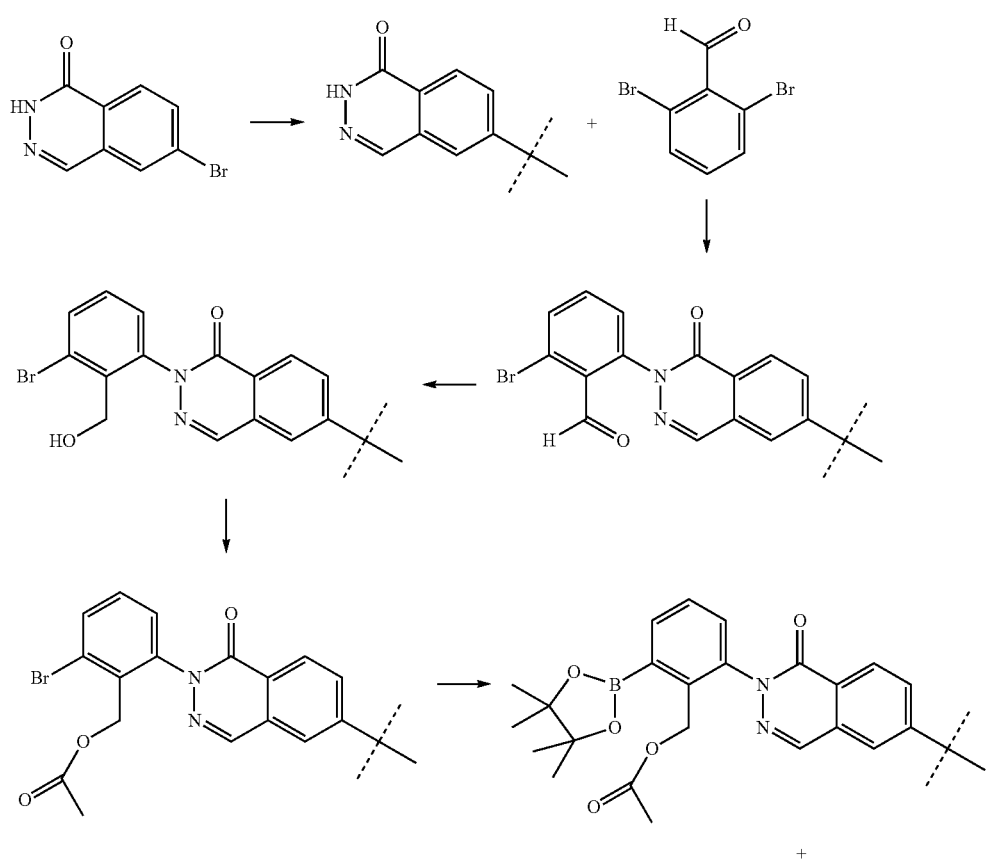

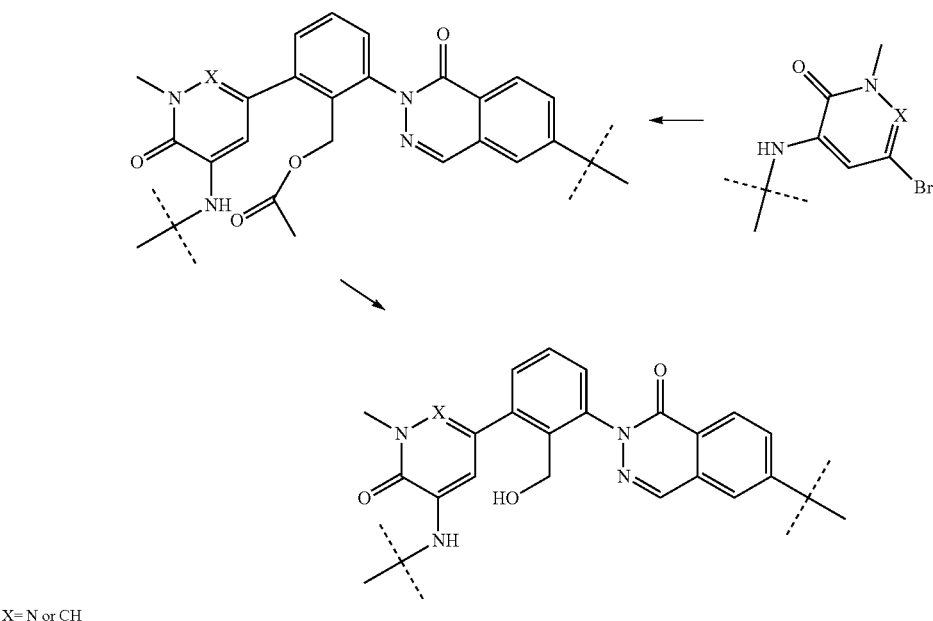

X= N or CH

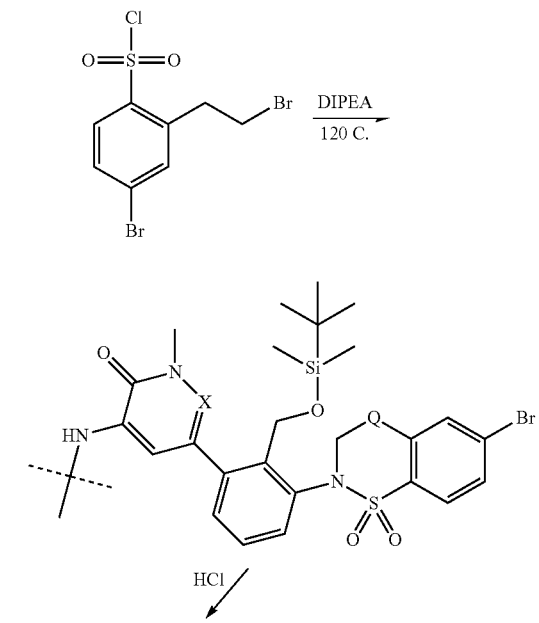

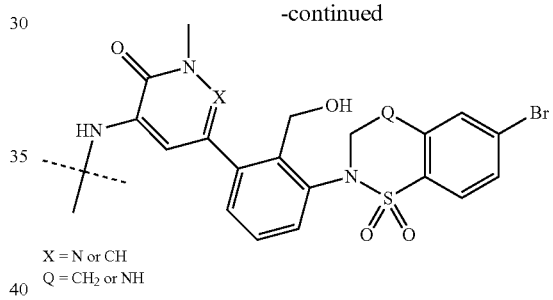

X = N or CH
Q = CH₂ or NH

Assay Data

Bruton's Tyrosine Kinase (Btk) Inhibition Assay

The assay is a capture of radioactive $^{33}$P phosphorylated product through filtration. The interactions of Btk, biotinylated SH$_2$ peptide substrate (Src homology), and ATP lead to phosphorylation of the peptide substrate. Biotinylated product is bound streptavidin sepharose beads. All bound, radio-labeled products are detected by scintillation counter.

Plates assayed are 96-well polypropylene (Greiner) and 96-well 1.2 µm hydrophilic PVDF filter plates (Millipore). Concentrations reported here are final assay concentrations: 10-100 µM compounds in DMSO (Burdick and Jackson), 5-10 nM Btk enzyme (His-tagged, full-length), 30 µM peptide substrate (Biotin-Aca-AAAEEIYGEI-NH$_2$), 100 µM ATP (Sigma), 8 mM imidazole (Sigma, pH 7.2), 8 mM glycerol-2-phosphate (Sigma), 200 µM EGTA (Roche Diagnostics), 1 mM MnCl$_2$ (Sigma), 20 mM MgCl$_2$ (Sigma), 0.1 mg/ml BSA (Sigma), 2 mM DTT (Sigma), 1 µCi $^{33}$P ATP (Amersham), 20% streptavidin sepharose beads (Amersham), 50 mM EDTA (Gibco), 2 M NaCl (Gibco), 2 M NaCl w/1% phosphoric acid (Gibco), microscint-20 (Perkin Elmer).

IC$_{50}$ determinations are calculated from 10 data points per compound utilizing data produced from a standard 96-well plate assay template. One control compound and seven unknown inhibitors were tested on each plate and each plate was run twice. Typically, compounds were diluted in half-log starting at 100 µM and ending at 3 nM. The control compound was staurosporine. Background was counted in the absence of peptide substrate. Total activity was determined in the presence of peptide substrate. The following protocol was used to determine Btk inhibition.

1) Sample preparation: The test compounds were diluted at half-log increments in assay buffer (imidazole, glycerol-2-phosphate, EGTA, $MnCl_2$, $MgCl_2$, BSA).
2) Bead preparation
   a.) rinse beads by centrifuging at 500 g
   b.) reconstitute the beads with PBS and EDTA to produce a 20% bead slurry
3) Pre-incubate reaction mix without substrate (assay buffer, DTT, ATP, $^{33}P$ ATP) and mix with substrate (assay buffer, DTT, ATP, $^{33}P$ ATP, peptide substrate) 30° C. for 15 min.
4) To start assay, pre-incubate 10 µL Btk in enzyme buffer (imidazole, glycerol-2-phosphate, BSA) and 10 µL of test compounds for 10 min at RT.
5) Add 30 µL reaction mixture without or with substrate to Btk and compounds.
6) Incubate 50 µL total assay mix for 30 min at 30° C.
7) Transfer 40 µL of assay to 150 µL bead slurry in filter plate to stop reaction.
8) Wash filter plate after 30 min, with following steps
   a. 3×250 µL NaCl
   b. 3×250 µL NaCl containing 1% phosphoric acid
   c. 1×250 µL $H_2O$
9) Dry plate for 1 h at 65° C. or overnight at RT
10) Add 50 µL microscint-20 and count $^{33}P$ cpm on scintillation counter.

Calculate percent activity from raw data in cpm percent activity=(sample–$bkg$)/(total activity–$bkg$)×100

Calculate $IC_{50}$ from percent activity, using one-site dose response sigmoidal model $y=A+((B-A)/(1+((x/C)^D)))$ x=cmpd conc, y=% activity, A=min, B=max, C=$IC_{50}$, D=1 (hill slope)

Representative results are in Table II below:

TABLE II

| Compound | Btk inhibition $IC_{50}$ (µM) |
|---|---|
| I-1 | 0.112 |
| II-1 | 0.022 |
| III-3 | 0.018 |
| III-1 | 0.124 |

Inhibition of B-Cell Activation

B Cell FLIPR Assay in Ramos Cells

Inhibition of B-cell activation by compounds of the present invention is demonstrated by determining the effect of the test compounds on anti-IgM stimulated B cell responses.

The B cell FLIPR assay is a cell based functional method of determining the effect of potential inhibitors of the intracellular calcium increase from stimulation by an anti-IgM antibody. Ramos cells (human Burkitt's lymphoma cell line. ATCC-No. CRL-1596) were cultivated in Growth Media (described below). One day prior to assay, Ramos cells were resuspended in fresh growth media (same as above) and set at a concentration of 0.5×10$^6$/mL in tissue culture flasks. On day of assay, cells are counted and set at a concentration of 1×10$^6$/mL1 in growth media supplemented with 1 µM FLUO-3 AM (TefLabs Cat-No. 0116, prepared in anhydrous DMSO and 10% Pluronic acid) in a tissue culture flask, and incubated at 37° C. (4% $CO_2$) for one h. To remove extracellular dye, cells were collected by centrifugation (5 min, 1000 rpm), resuspended in FLIPR buffer (described below) at 1×10$^6$ cells/mL and then dispensed into 96-well poly-D-lysine coated black/clear plates (BD Cat-No. 356692) at 1×10$^5$ cells per well. Test compounds were added at various concentrations ranging from 100 µM to 0.03 µM (7 concentrations, details below), and allowed to incubate with cells for 30 min at RT. Ramos cell $Ca^{2+}$ signaling was stimulated by the addition of 10 µg/mL anti-IgM (Southern Biotech, Cat-No. 2020-01) and measured on a FLIPR (Molecular Devices, captures images of 96 well plates using a CCD camera with an argon laser at 480 nM excitation).

Media/Buffers:

Growth Medium: RPMI 1640 medium with L-glutamine (Invitrogen, Cat-No. 61870-010), 10% Fetal Bovine Serum (FBS, Summit Biotechnology Cat-No. FP-100-05); 1 mM Sodium Pyruvate (Invitrogen Cat. No. 11360-070).

FLIPR buffer: HBSS (Invitrogen, Cat-No. 141175-079), 2 mM $CaCl_2$ (Sigma Cat-No. C-4901), HEPES (Invitrogen, Cat-No. 15630-080), 2.5 mM Probenecid (Sigma, Cat-No. P-8761), 0.1% BSA (Sigma, Cat-No. A-7906), 11 mM Glucose (Sigma, Cat-No. G-7528)

Compound Dilution Details:

In order to achieve the highest final assay concentration of 100 µM, 24 µL of 10 mM compound stock solution (made in DMSO) is added directly to 576 µL of FLIPR buffer. The test compounds are diluted in FLIPR Buffer (using Biomek 2000 robotic pipetter) resulting in the following dilution scheme: vehicle, 1.00×10$^{-4}$ M, 1.00×10$^{-5}$, 3.16×10$^{-6}$, 1.00×10$^{-6}$, 3.16×10$^{-7}$, 1.00×10$^{-7}$, 3.16×10$^{-8}$.

Assay and Analysis:

Intracellular increases in calcium were reported using a max-min statistic (subtracting the resting baseline from the peak caused by addition of the stimulatory antibody using a Molecular Devices FLIPR control and statistic exporting software. The $IC_{50}$ was determined using a non-linear curve fit (GraphPad Prism software).

Mouse In Vivo Collagen-Induced Arthritis (mCIA)

On day 0 mice are injected at the base of the tail or several spots on the back with an emulsion of Type II Collagen (i.d.) in Complete Freund's adjuvant (CFA). Following collagen immunization, animals will develop arthritis at around 21 to 35 days. The onset of arthritis is synchronized (boosted) by systemic administration of collagen in Incomplete Freund's adjuvant (IFA; i.d.) at day 21. Animals are examined daily after day 20 for any onset of mild arthritis (score of 1 or 2; see score description below) which is the signal to boost. Following boost, mice are scored and dosed with candidate therapeutic agents for the prescribed time (typically 2-3 weeks) and dosing frequency, daily (QD) or twice-daily (BID).

Rat In Vivo Collagen-Induced Arthritis (rCIA)

On day 0, rats are injected with an emulsion of Bovine Type II Collagen in Incomplete Freund's adjuvant (IFA) is injected intradermally (i.d.) on several locations on the back. A booster injection of collagen emulsion is given around day 7, (i.d.) at the base of the tail or alternative sites on the back. Arthritis is generally observed 12-14 days after the initial collagen injection. Animals may be evaluated for the development of arthritis as described below (Evaluation of arthritis) from day 14 onwards. Animals are dosed with candidate therapeutic agents in a preventive fashion starting at the time of secondary challenge and for the prescribed time (typically 2-3 weeks) and dosing frequency, daily (QD) or twice-daily (BID).

Evaluation of Arthritis:

In both models, developing inflammation of the paws and limb joints is quantified using a scoring system that involves the assessment of the 4 paws following the criteria described below:

Scoring: 1=swelling and/or redness of paw or one digit.
    2=swelling in two or more joints.
    3=gross swelling of the paw with more than two joints involved.
    4=severe arthritis of the entire paw and digits.

Evaluations are made on day 0 for baseline measurement and starting again at the first signs or swelling for up to three times per week until the end of the experiment. The arthritic index for each mouse is obtained by adding the four scores of the individual paws, giving a maximum score of 16 per animal.

Rat In Vivo Asthma Model

Male Brown-Norway rats are sensitized i.p. with 100 μg of OA (ovalbumin) in 0.2 ml alum once every week for three weeks (day 0, 7, and 14). On day 21 (one week following last sensitization), the rats are dosed q.d. with either vehicle or compound formulation subcutaneously 0.5 hour before OA aerosol challenge (1% OA for 45 minutes) and terminated 4 or 24 hours after challenge. At time of sacrifice, serum and plasma are collected from all animals for serology and PK, respectively. A tracheal cannula is inserted and the lungs are lavaged 3× with PBS. The BAL fluid is analyzed for total leukocyte number and differential leukocyte counts. Total leukocyte number in an aliquot of the cells (20-100 μl) is determined by Coulter Counter. For differential leukocyte counts, 50-200 μl of the sample is centrifuged in a Cytospin and the slide stained with Diff-Quik. The proportions of monocytes, eosinophils, neutrophils and lymphocytes are counted under light microscopy using standard morphological criteria and expressed as a percentage. Representative inhibitors of Btk show decreased total leucocyte count in the BAL of OA sensitized and challenged rats as compared to control levels.

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation (F) | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:
1. A compound of Formula I,

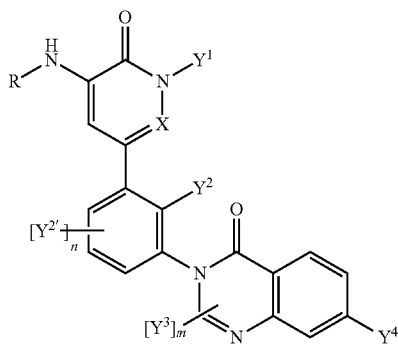

I wherein:
R is H, —$R^1$, —$R^1$—$R^2$—$R^3$, —$R^1$—$R^3$, or —$R^2$—$R^3$;
  $R^1$ is aryl, heteroaryl, cycloalkyl, or heterocycloalkyl, and is optionally substituted with $R^{1'}$;
  $R^{1'}$ is lower alkyl, hydroxy, lower hydroxyalkyl, lower alkoxy, halogen, nitro, amino, cycloalkyl, heterocycloalkyl, cyano, or lower haloalkyl;
  $R^2$ is —C(=O), —C(=O)O, —C(=O)N($R^{2'}$), —$(CH_2)_q$, or —S(=O)$_2$;
  $R^{2'}$ is H or lower alkyl;
  q is 1, 2, or 3;
  $R^3$ is H or $R^4$;
  $R^4$ is lower alkyl, lower alkoxy, lower heteroalkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with one or more lower alkyl, hydroxy, oxo, lower hydroxyalkyl, lower alkoxy, halogen, nitro, amino, cyano, lower alkylsulfonyl, or lower haloalkyl;
X is CH or N;
$Y^1$ is H or lower alkyl;
$Y^2$ is $Y^{2a}$ or $Y^{2b}$;
  $Y^{2a}$ is H or halogen;
  $Y^{2b}$ is lower alkyl, substituted with one or more $Y^{2b'}$;
    $Y^{2b'}$ is hydroxy, lower alkoxy, or halogen;
each $Y^{2'}$ is independently $Y^{2'a}$ or $Y^{2'b}$;
  $Y^{2'a}$ is halogen;
  $Y^{2'b}$ is lower alkyl, optionally substituted with one or more $Y^{2'b'}$;
    $Y^{2'b'}$ is hydroxy, lower alkoxy, or halogen;
n is 0, 1, 2, or 3;
$Y^3$ is H, halogen, or lower alkyl, wherein lower alkyl is optionally substituted with one or more substituents selected from the group consisting of hydroxy, lower alkoxy, amino, and halogen;
m is 0 or 1;
$Y^4$ is $Y^{4a}$, $Y^{4b}$, $Y^{4c}$, or $Y^{4d}$;
  $Y^{4a}$ is H or halogen;
  $Y^{4b}$ is lower alkyl, optionally substituted with one or more substituents selected from the group consisting of lower haloalkyl, halogen, hydroxy, amino, cyano and lower alkoxy;
  $Y^{4c}$ is lower cycloalkyl, optionally substituted with one or more substituents selected from the group consisting of lower alkyl, lower haloalkyl, halogen, hydroxy, amino, and lower alkoxy; and
  $Y^{4d}$ is amino, optionally substituted with one or more lower alkyl;
or a pharmaceutically acceptable salt thereof.
2. The compound of claim 1, wherein $Y^1$ is methyl.
3. The compound of claim 2, wherein X is CH.
4. The compound of claim 3, wherein n is 0.
5. The compound of claim 4, wherein m is 0.
6. The compound of claim 5, wherein $Y^2$ is hydroxymethyl.
7. The compound of claim 6, wherein $Y^4$ is

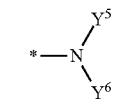

wherein, $Y^5$ is H, halogen, lower alkyl, or lower haloalkyl.
8. The compound of claim 6, wherein $Y^4$ is

*—⟨OH, $Y^5$, $Y^6$⟩ wherein, $Y^5$ and $Y^6$ are independently H, lower alkyl, or lower haloalkyl.
9. The compound of claim 6, wherein $Y^4$ is

*—N⟨$Y^5$, $Y^6$⟩ wherein, $Y^5$ and $Y^6$ are independently H or lower alkyl.

10. The compound of claim 6, wherein $Y^4$ is

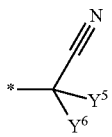

wherein, $Y^5$ and $Y^6$ are independently H, lower alkyl, or lower haloalkyl.

11. The compound of claim 7, wherein
R is —$R^1$—$R^2$—$R^3$;
$R^1$ is phenyl or pyridyl;
$R^2$ is —C(=O);
$R^3$ is $R^4$; and
$R^4$ is morpholine or piperazine, optionally substituted with one or more lower alkyl.

12. A compound of Formula II,

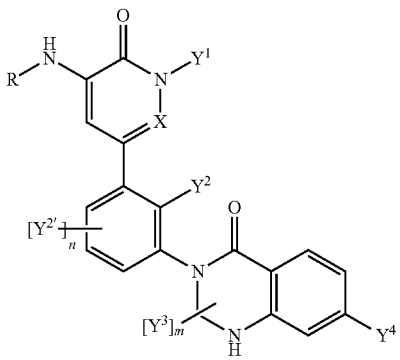

II wherein:
R is H, —$R^1$, —$R^1$—$R^2$—$R^3$, —$R^1$—$R^3$, or —$R^2$—$R^3$;
  $R^1$ is aryl, heteroaryl, cycloalkyl, or heterocycloalkyl, and is optionally substituted with $R^{1'}$;
  $R^{1'}$ is lower alkyl, hydroxy, lower hydroxyalkyl, lower alkoxy, halogen, nitro, amino, cycloalkyl, heterocycloalkyl, cyano, or lower haloalkyl;
  $R^2$ is —C(=O), —C(=O)O, —C(=O)N($R^{2'}$), —$(CH_2)_q$, or —S(=O)$_2$;
  $R^{2'}$ is H or lower alkyl;
  q is 1, 2, or 3;
  $R^3$ is H or $R^4$;
  $R^4$ is lower alkyl, lower alkoxy, lower heteroalkyl, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, or heterocycloalkyl alkyl, and is optionally substituted with one or more lower alkyl, hydroxy, oxo, lower hydroxyalkyl, lower alkoxy, halogen, nitro, amino, cyano, lower alkylsulfonyl, or lower haloalkyl;
X is CH or N;
$Y^1$ is H or lower alkyl;
$Y^2$ is $Y^{2a}$ or $Y^{2b}$;
  $Y^{2a}$ is H or halogen;
  $Y^{2b}$ is lower alkyl, optionally substituted with one or more $Y^{2b'}$;
  $Y^{2b'}$ is hydroxy, lower alkoxy, or halogen;
each $Y^{2'}$ is independently $Y^{2'a}$ or $Y^{2'b}$;
  $Y^{2'a}$ is halogen;
  $Y^{2'b}$ is lower alkyl, optionally substituted with one or more $Y^{2'b'}$;
  $Y^{2'b'}$ is hydroxy, lower alkoxy, or halogen;
n is 0, 1, 2, or 3;
$Y^3$ is H, halogen, or lower alkyl, wherein lower alkyl is optionally substituted with one or more substituents selected from the group consisting of hydroxy, lower alkoxy, amino, and halogen;
m is 0 or 1;
$Y^4$ is $Y^{4a}$, $Y^{4b}$, $Y^{4c}$, or $Y^{4d}$;
  $Y^{4a}$ is H or halogen;
  $Y^{4b}$ is lower alkyl, optionally substituted with one or more substituents selected from the group consisting of lower haloalkyl, halogen, hydroxy, amino, cyano and lower alkoxy;
  $Y^{4c}$ is lower cycloalkyl, optionally substituted with one or more substituents selected from the group consisting of lower alkyl, lower haloalkyl, halogen, hydroxy, amino, and lower alkoxy; and
  $Y^{4d}$ is amino, optionally substituted with one or more lower alkyl;
or a pharmaceutically acceptable salt thereof.

13. The compound of claim 12, wherein $Y^1$ is methyl.

14. The compound of claim 13, wherein X is CH.

15. The compound of claim 14, wherein n is 0.

16. The compound of claim 15, wherein m is 0.

17. The compound of claim 16, wherein $Y^2$ is hydroxymethyl.

18. The compound of claim 17, wherein $Y^4$ is

wherein, $Y^5$ is H, halogen, lower alkyl, or lower haloalkyl.

19. A compound selected from the group consisting of:
1-{5-[3-(7-tert-Butyl-4-oxo-4H-quinazolin-3-yl)-2-methyl-phenyl]-1-methyl-2-oxo-1,2-dihydro-pyridin-3-yl}-3-methyl-urea;
7-Dimethylamino-3-(2-methyl-3-{1-methyl-5-[5-(morpholine-4-carbonyl)-pyridin-2-ylamino]-6-oxo-1,6-dihydro-pyridin-3-yl}-phenyl)-3H-quinazolin-4-one;
7-Dimethylamino-3-(2-methyl-3-{1-methyl-5-[5-(morpholine-4-carbonyl)-pyridin-2-ylamino]-6-oxo-1,6-dihydro-pyridin-3-yl}-phenyl)-2,3-dihydro-1H-quinazolin-4-one;
1-{5-[3-(7-Dimethylamino-4-oxo-1,4-dihydro-2H-quinazolin-3-yl)-2-methyl-phenyl]-1-methyl-2-oxo-1,2-dihydro-pyridin-3-yl}-3-methyl-urea; and
7-(1-Hydroxy-1-methyl-ethyl)-3-(2-methyl-3-{1-methyl-5-[5-(morpholine-4-carbonyl)-pyridin-2-ylamino]-6-oxo-1,6-dihydro-pyridin-3-yl}-phenyl)-2,3-dihydro-1H-quinazolin-4-one.

20. A method for treating rheumatoid arthritis comprising administering to a patient in need thereof a therapeutically effective amount of the Btk inhibitor compound of claim 1.

21. A method for treating rheumatoid arthritis comprising administering to a patient in need thereof a therapeutically effective amount of the Btk inhibitor compound of claim 12.

22. A method for treating asthma comprising administering to a patient in need thereof a therapeutically effective amount of the Btk inhibitor compound of claim 1.

23. A method for treating asthma comprising administering to a patient in need thereof a therapeutically effective amount of the Btk inhibitor compound of claim 12.

* * * * *

UNITED STATES PATENT AND TRADEMARK OFFICE
CERTIFICATE OF CORRECTION

PATENT NO. : 8,124,604 B2  
APPLICATION NO. : 12/987187  
DATED : February 28, 2012  
INVENTOR(S) : Dewdney et al.

Page 1 of 1

It is certified that error appears in the above-identified patent and that said Letters Patent is hereby corrected as shown below:

Claim 20, column 94, line 53, delete "treating" and insert -- the therapeutic treatment of --
Claim 20, column 94, line 55, delete "Btk inhibitor"

Claim 21, column 94, line 56, delete "treating" and insert -- the therapeutic treatment of --
Claim 21, column 94, line 58, delete "Btk inhibitor"

Claim 22, column 94, line 59, delete "treating" and insert -- the therapeutic treatment of --
Claim 22, column 94, line 61, delete "Btk inhibitor"

Claim 23, column 94, line 62, delete "treating" and insert -- the therapeutic treatment of --
Claim 23, column 94, line 64, delete "Btk inhibitor"

Signed and Sealed this
Eighth Day of May, 2012

David J. Kappos
*Director of the United States Patent and Trademark Office*